(12) United States Patent
Carpenter et al.

(10) Patent No.: US 11,045,297 B2
(45) Date of Patent: Jun. 29, 2021

(54) TOPOGRAPHICAL FEATURES AND PATTERNS ON A SURFACE OF A MEDICAL DEVICE AND METHODS OF MAKING THE SAME

(71) Applicant: Palmaz Scientific, Inc., Dallas, TX (US)

(72) Inventors: Scott Carpenter, Fremont, CA (US); Michael Poor, Fremont, CA (US); Julio C. Palmaz, Napa, CA (US)

(73) Assignee: VACTRONIX SCIENTIFIC LLC, Fremont, CA (US)

( * ) Notice: Subject to any disclaimer, the term of this patent is extended or adjusted under 35 U.S.C. 154(b) by 0 days.

(21) Appl. No.: 13/801,173

(22) Filed: Mar. 13, 2013

(65) Prior Publication Data

US 2014/0114435 A1    Apr. 24, 2014

Related U.S. Application Data

(63) Continuation-in-part of application No. 13/654,923, filed on Oct. 18, 2012, now Pat. No. 9,050,394.

(51) Int. Cl.
*A61F 2/00* (2006.01)
*A61F 2/82* (2013.01)
*A61F 2/915* (2013.01)
*A61F 2/24* (2006.01)

(52) U.S. Cl.
CPC .............. *A61F 2/0077* (2013.01); *A61F 2/24* (2013.01); *A61F 2/82* (2013.01); *A61F 2/915* (2013.01); *A61F 2002/0081* (2013.01); *Y10T 29/49982* (2015.01)

(58) Field of Classification Search
CPC .......... A61F 2/0077; A61F 2/82; A61F 2/915; A61F 2002/0081; A61F 2/24; A61F 2/02; Y10S 623/901; C23F 1/02; B29C 33/56; B29C 234/185; C23C 4/185; Y10T 29/49982; B21D 17/00; B81C 1/00206
USPC ....... 29/527.2; 623/1.15, 1.16, 901; 430/320
See application file for complete search history.

(56) References Cited

U.S. PATENT DOCUMENTS

| | | | |
|---|---|---|---|
| 4,733,665 A | 3/1988 | Palmaz | 128/343 |
| 5,102,417 A | 4/1992 | Palmaz | 606/195 |
| 5,195,984 A | 3/1993 | Schatz | 606/195 |
| 5,855,802 A | 1/1999 | Acciai et al. | 216/8 |

(Continued)

FOREIGN PATENT DOCUMENTS

| | | | | |
|---|---|---|---|---|
| JP | 2007-526032 | 9/2007 | ............... | A61F 2/84 |
| JP | 2010516432 | 5/2010 | ............... | A61L 2/82 |

(Continued)

OTHER PUBLICATIONS

Hehriein, et. al., "Influence of surface texture and charge on the biocompatibility of endovascular stents" *Coronary Artery Disease* 6: 581-586 (1995).

(Continued)

*Primary Examiner* — Lee A Holly
(74) *Attorney, Agent, or Firm* — David G. Rosenbaum; Rosenbaum IP, P.C.

(57) ABSTRACT

The invention relates to medical devices that has a surface configured to promote the migration of cells onto the surface of the medical device. In particular, the surface of the medical device has a noncontiguous pattern of topographical features formed therein or thereon.

8 Claims, 19 Drawing Sheets

(56) References Cited

U.S. PATENT DOCUMENTS

| | | | | |
|---|---|---|---|---|
| 6,027,863 | A | 2/2000 | Donadio, III | 430/320 |
| 6,146,814 | A | 11/2000 | Millet | 430/320 |
| 6,190,404 | B1 | 2/2001 | Palmaz et al. | 623/1.15 |
| 6,379,383 | B1 | 4/2002 | Palmaz et al. | 623/1.49 |
| 6,685,737 | B1 * | 2/2004 | Pacetti | A61F 2/86 |
| | | | | 623/1.15 |
| 6,820,676 | B2 | 11/2004 | Palmaz et al. | 164/46 |
| 7,650,848 | B2 * | 1/2010 | Brennan | B81C 1/00206 |
| | | | | 114/222 |
| 8,329,021 | B2 | 12/2012 | Garza | 205/666 |
| 2002/0017503 | A1 * | 2/2002 | Banas | C23F 1/02 |
| | | | | 219/69.11 |
| 2003/0216803 | A1 | 11/2003 | Ledergerber | 623/1.13 |
| 2004/0236398 | A1 | 11/2004 | Burgmeier et al. | 623/1.11 |
| 2005/0014151 | A1 * | 1/2005 | Textor et al. | 435/6 |
| 2005/0209684 | A1 * | 9/2005 | Alexander et al. | 623/1.15 |
| 2005/0232968 | A1 * | 10/2005 | Palmaz | A61F 2/02 |
| | | | | 424/423 |
| 2008/0183276 | A1 | 7/2008 | Melder | 623/1.15 |
| 2008/0299337 | A1 | 12/2008 | Glocker et al. | 428/34.1 |
| 2009/0035859 | A1 | 2/2009 | Johnson | 435/402 |
| 2009/0093879 | A1 | 4/2009 | Wawro et al. | 623/11.11 |
| 2009/0304772 | A1 | 12/2009 | Choubey et al. | 424/423 |
| 2010/0226943 | A1 | 9/2010 | Brennan et al. | 424/400 |
| 2011/0264190 | A1 * | 10/2011 | McClain et al. | 623/1.11 |
| 2011/0276125 | A1 * | 11/2011 | Walker | G03B 27/52 |
| | | | | 623/1.15 |
| 2012/0109285 | A1 | 5/2012 | Garza | 623/1.46 |
| 2012/0132612 | A1 * | 5/2012 | Banas et al. | 216/8 |
| 2012/0232649 | A1 | 9/2012 | Cuevas | 623/6.16 |
| 2012/0290074 | A1 | 11/2012 | Palmaz | 623/1.36 |

FOREIGN PATENT DOCUMENTS

| | | | | |
|---|---|---|---|---|
| WO | WO 1999/061261 | 12/1999 | | B44C 1/22 |
| WO | WO 2008/061185 | 5/2008 | | A61F 2/24 |
| WO | WO 2009/123624 | 10/2009 | | A61F 2/90 |

OTHER PUBLICATIONS

Palmaz, J., "The impact of material science and nanotechnology on device innovation in cardiovascular medicine" *TCT* pp. 1-89 (2010).
Sprague, E., "Impact of stent surface texture and strut thickness: experimental and clinical evidence" *TCT* pp. 1-16 (2010).
PCT International Search Report for PCT/US2013/065324, filed Oct. 16, 2013, and published on Apr. 24, 2014 as WO 2014-062854, 5 pages.
PCT International Search Report issued in corresponding foreign application, pp. 1-5 (dated Jun. 9, 2014).
PCT Preliminary Report on Patentability issued in corresponding foreign application, pp. 1-8 (dated Sep. 24, 2015).
EP Search Report issued in corresponding foreign application, pp. 1-7 (dated May 13, 2016).
Extended EP Search Report issued in corresponding foreign application, pp. 1-7 (dated Oct. 19, 2016).
Examination report No. 1 issued in related foreign application, AU 2014242126, pp. 1-4 (dated Aug. 23, 2017).
Notice of Non-Final Rejection issued in related foreign application, JP 2016-500367, pp. 1-3 (dated Feb. 1, 2018).
Examination report No. 2 issued in related foreign application, AU 2014242126, pp. 1-4 (dated Aug. 20, 2018).
Notice of Non-Final Rejection issued in related foreign application, JP 2016-500367, pp. 1-4 (dated Dec. 11, 2018).
Examination report No. 1 issued in related foreign application, AU 2018220082, pp. 1-3 (dated Jun. 13, 2019).
Communication pursuant to Article 94(3) EPC issued in related foreign application, EP 13847874.8, pp. 143 (dated Jul. 16, 2019).
Office Action issued in related foreign application, CA 2,905,251, pp. 1-5 (dated Feb. 5, 2020).
Office Action issued in related foreign application, CA 2,888,925, pp. 1-4 (dated Oct. 8, 2019).
Notice of Decision for Rejection in related foreign application, JP 2016-500367, pp. 1-4 (dated Nov. 5, 2019).

* cited by examiner

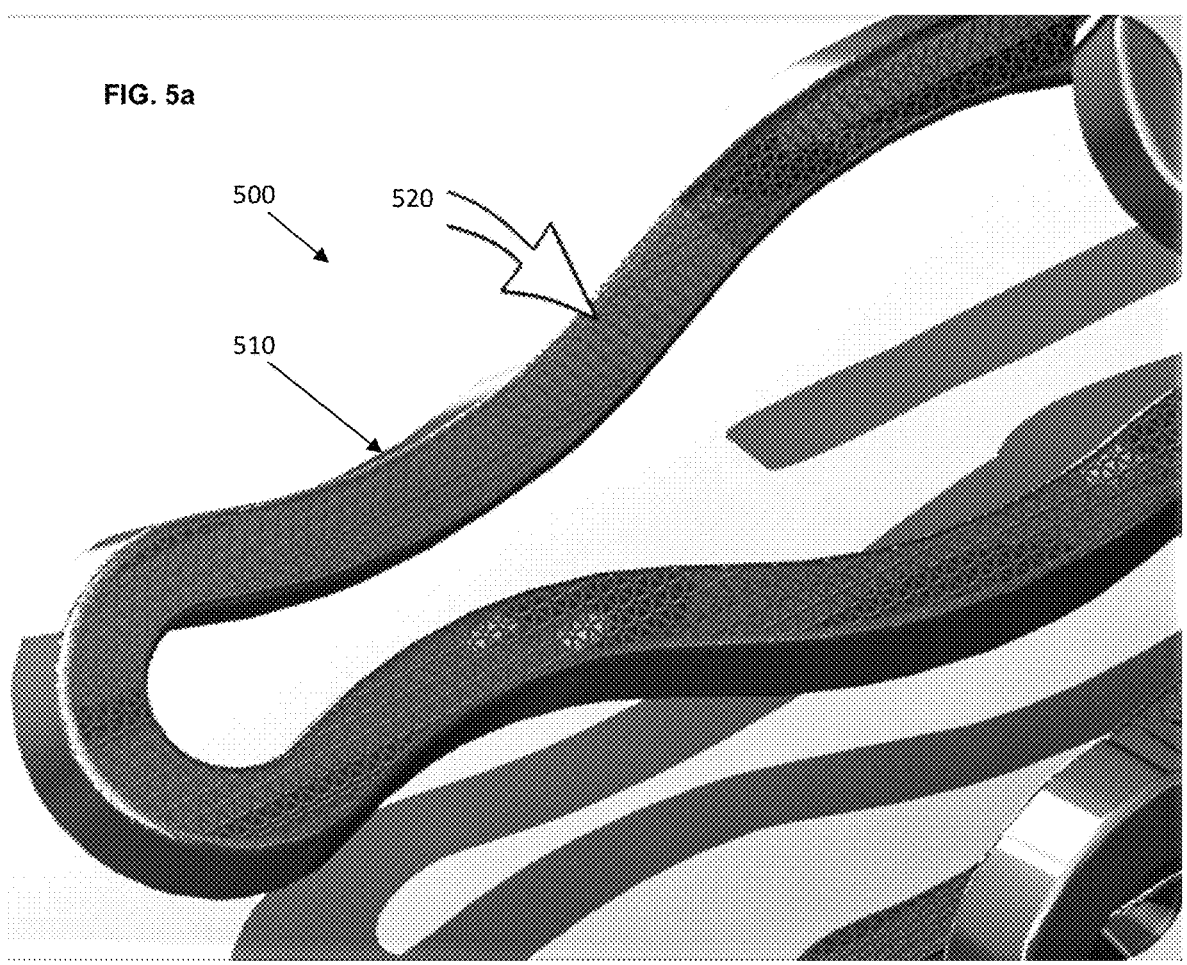

TOPOGRAPHICAL FEATURES AND PATTERNS ON A SURFACE OF A MEDICAL DEVICE AND METHODS OF MAKING THE SAME

CROSS REFERENCE TO RELATED APPLICATIONS

The present application is a continuation-in-part of U.S. patent application Ser. No. 13/654,923, filed Oct. 18, 2012, which is hereby incorporated by reference in its entirety.

The present application is related to co-pending and commonly owned U.S. patent application Ser. No. 13/103,576, filed May 9, 2011, which is hereby incorporated by reference in its entirety.

BACKGROUND OF THE INVENTION

The invention relates to methods and apparatus for manufacturing medical devices, wherein the medical device has a surface treated to promote the migration of cells onto the surface of the medical device.

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Intravascular stents are used, in general, as a mechanical means to solve the most common problems of percutaneous balloon angioplasty, such as elastic recoil and intimal dissection. One problem intraluminal stent placement shares with other revascularization procedures, including bypass surgery and balloon angioplasty, is restenosis of the artery. An important factor contributing to this possible reocclusion at the site of stent placement is injury to, and loss of, the natural nonthrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Depending on a multitude of factors, such as activity of the fibrinolytic system, the use of anticoagulants, and the nature of the lesion substrate, the result of this process may range from a small mural to an occlusive thrombus. Secondly, loss of the endothelium at the interventional site may be critical to the development and extent of eventual intimal hyperplasia at the site. Previous studies have demonstrated that the presence of an intact endothelial layer at an injured arterial site can significantly inhibit the extent of smooth muscle cell-related intimal hyperplasia. Rapid re-endothelialization of the arterial wall, as well as endothelialization of the prosthetic surface, or inner surface of the stent, are therefore critical for the prevention of low-flow thrombosis and for continued patency. Unless endothelial cells from another source are somehow introduced and seeded at the site, coverage of an injured area of endothelium is achieved primarily, at least initially, by migration of endothelial cells from adjacent arterial areas of intact endothelium.

Although an in vitro biological coating to a stent in the form of seeded endothelial cells on metal stents has been previously proposed, there are believed to be serious logistic problems related to live-cell seeding, which may prove to be insurmountable. Thus, it would be advantageous to increase the rate at which endothelial cells from adjacent arterial areas of intact endothelium migrate upon the inner surface of the stent exposed to the flow of blood through the artery. At present, most intravascular stents are manufactured of stainless steel and such stents become embedded in the arterial wall by tissue growth weeks to months after placement. This favorable outcome occurs consistently with any stent design, provided it has a reasonably low metal surface and does not obstruct the fluid, or blood, flow through the artery. Furthermore, because of the fluid dynamics along the inner arterial walls caused by blood pumping through the arteries, along with the blood/endothelium interface itself, it has been desired that the stents have a very smooth surface to facilitate migration of endothelial cells onto the surface of the stent. In fact, it has been reported that smoothness of the stent surface after expansion is crucial to the biocompatibility of a stent, and thus, any surface topography other than smooth is not desired. Christoph Hehriein, et. al., Influence of Surface Texture and Charge On the Biocompatibility of Endovascular Stents, Coronary Artery Disease, Vol. 6, pages 581-586 (1995). After the stent has been coated with serum proteins, the endothelium grows over the fibrin-coated metal surface on the inner surface of the stent until a continuous endothelial layer covers the stent surface, in days to weeks. Endothelium renders the thrombogenic metal surface protected from thrombus deposition, which is likely to form with slow or turbulent flow. At present, all intravascular stents made of stainless steel, or other alloys or metals, are provided with an extremely smooth surface finish, such as is usually obtained by electropolishing the metallic stent surfaces. Although presently known intravascular stents, specific including the Palmaz™ and Palmaz-Schatz™ balloon-expandable stents have been demonstrated to be successful in the treatment of coronary disease, as an adjunct to balloon angioplasty, intravascular stents could be even more successful and efficacious, if the rate and/or speed of endothelial cell migration onto the inner surface of the stent could be increased.

However, known topographical features, e.g., grooves, impart the greatest benefit when the features are placed parallel with blood flow across a medical device. No benefit from the topographical features is realized when the features are oriented perpendicular to the flow of blood.

Still further, maintaining this optimal orientation of the features can be problematic for continuous features, since the final shape and orientation can depend on many factors. When the medical device is a stent, the final shape, and expansion size, can vary depending on the condition, size, shape, and compliance of the blood vessel where the stent is implanted. Similar implantation site factors can affect the orientation of topographical features on other implanted medical devices.

The present invention attempts to solve this problem, and others.

SUMMARY OF THE INVENTION

In accordance with the embodiments disclosed herein, at least one noncontiguous pattern of topographical features is disposed in or on a surface of the device. The noncontiguous pattern of topographical features allows for cell migration in more than one direction, thus permitting endothelial cells to migrate in the direction of blood flow, regardless of the final positioning of the medical device.

In one embodiment, there is provided a method of manufacturing a medical device by first forming a device having at least one surface; and then forming at least one noncontiguous pattern of topographical features in or on the surface of the device. The device may be any implantable medical device, such as a stent.

Any type of cell is encompassed by the present invention, which cell has a cellular membrane.

In accordance with the embodiments disclosed herein, the capacity for complete cell coverage of conventional implantable materials, including metals and polymers, may be enhanced by imparting a noncontiguous pattern of chemically and/or physiochemically active geometric physiologically functional features onto a blood contacting surface of the implantable material. The inventive implantable devices may be fabricated of polymers, pre-existing conventional wrought metallic materials, such as stainless steel or nitinol hypotubes.

In any embodiment, an existing medical device, stent, or other article may be utilized. Through the use of an existing structure, it is likely that the regulatory path may be minimized. Particular, non-limiting devices include dental implants and hip implants.

The noncontiguous pattern of topographical features, when compared with presently known devices and methods for manufacturing such devices, improves the control of various cell responses at the surface of the medical device.

BRIEF DESCRIPTION OF THE DRAWINGS

FIG. 5a is an illustration of one embodiment of a stent having a noncontiguous pattern of topographical features imparted in an inner surface of the stent; FIG. 5b is a close up view of a portion of FIG. 5a.

FIG. 11b is an enlarged view of a portion of the dental implant of FIG. 11a.

FIG. 12b is an enlarged view of a portion of the hip implant of FIG. 12a; and FIG. 12c is an enlarged view of a distal portion of the hip implant of FIG. 12a.

FIG. 13b is an enlarged view of a portion of the heart valve of FIG. 13a.

Figure 1:
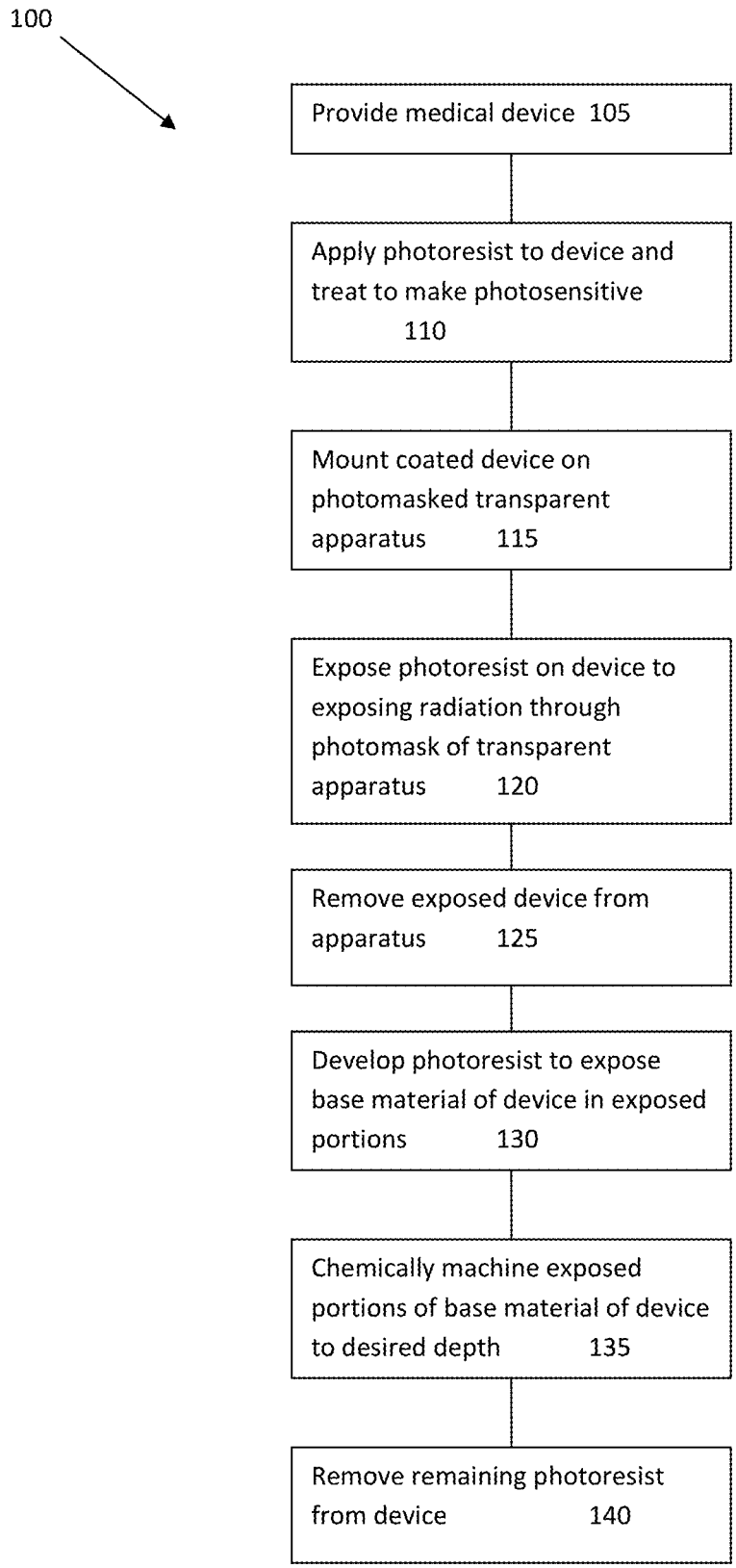
FIG. 1 is a block diagram illustrating a method of manufacturing a medical device having at least one noncontiguous pattern of topographical features created in or on a surface thereof.

While the invention will be described in connection with the preferred embodiment, it will be understood that it is not intended to limit the invention of that embodiment. On the contrary, it is intended to cover all alternatives, modifications, and equivalents, as may be included within the spirit and scope of the invention as defined by the appended claims.

DETAILED DESCRIPTION OF THE INVENTION

In one embodiment, the formation of the noncontiguous pattern of topographical features may be by etching the surface with a chemical process. Preferably, the chemical process may comprise the steps of coating the surface of the device with a photosensitive material; mounting the device on a mask; irradiating the surface of the device by a source of exposing radiation; removing the device from the mask; and etching light exposed areas to produce at least one noncontiguous pattern of topographical features in or on the surface of the device. The mask may be disposed upon a surface of a transparent apparatus adapted to have the device mounted thereupon, and the device is mounted on the transparent apparatus. The source of exposing radiation may be an ultraviolet light source, but could be a light source with any wavelength compatible with the photosensitive material. Alternatively, the exposing radiation may be atomic in nature. The exposing radiation may be transmitted through one edge of the apparatus, or transmitted by means of a fiber optic cable inserted within the apparatus below the mask. If a fiber optic cable is used, either an end transmitting fiber optic cable may be translated within the apparatus to gain even exposures, or a bare (preferably frosted) fiber may be used to broadcast the exposing radiation from within the apparatus. After exposure, the device is removed from the apparatus. The photosensitive material is developed to reveal the pattern imparted by the mask by exposing the base material of the device through the use of appropriate chemicals. The exposed base material of the device may then be chemically machined to a desired depth. The machining may be accomplished by wet or dry chemical etching or polishing, or by electrochemical machining.

The process will be able to follow the contours of the device by patterning. For example, the mask pattern can be created such that the groove pattern is altered to allow for the expansion of the stent such that the grooves are parallel to bloodflow after expansion by accounting for the deformation pattern of the stent. Alternatively, patterns can be tailored to steer cells in a particular direction. Any 2D or 3D pattern can be effectively embossed or debossed (or combination of both) in the surface. Alternatively, other methods may be used to create the mask, including, but not limited to electrical discharge machining, dry etching, photodegradation, waterjet, abrasive blasting to create the mask pattern. Additive methods are feasible as well where the masking material is added to the translucent member. An example of an additive method is inkjet technology to deposit a coating selectively to create a pattern that would block the light transmission. Any material that can block the exposure wavelength can be used as the mask, including metals, pseudometals, intermetallics, ceramics, polymers, and the like.

Although photolithography methodologies are discussed herein as a method of forming the noncontiguous pattern of topographical features, the present invention is not so limited. Any methodology to form the noncontiguous pattern of topographical features may be utilized, including photolithography, mechanical transfer, electrochemical machining, laser etching, electric discharge machining, and/or any other means of applying the pattern to a surface of the medical device. Generally, the present invention may comprise forming or providing a medical device having at least one surface and forming at least one noncontiguous pattern of topographical features in or on said surface.

Any type of cell is encompassed by the present invention, which cell has a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (cross-wise partitions) and mesenteries (length-wise partitions); and forms part of the gonads (the rest being the gametes).

In accordance with the embodiments disclosed herein, the capacity for complete cell coverage of conventional implantable materials, including metals and polymers, may be enhanced by imparting a noncontiguous pattern of chemically and/or physiochemically active geometric physiologically functional features onto a blood contacting surface of the implantable material. The inventive implantable devices may be fabricated of polymers, pre-existing conventional wrought metallic materials, such as stainless steel or nitinol hypotubes.

The inventive implantable devices may be intravascular stents, stent-grafts, grafts, heart valves, venous valves, filters, occlusion devices, catheters, sheaths, osteal implants, implantable contraceptives, implantable antitumor pellets or rods, shunts and patches, pacemakers, needles, temporary fixation rods, medical wires or medical tubes for any type of medical device, or other implantable medical devices, as will also be hereinafter described. A pacemaker (or artificial pacemaker, so as not to be confused with the heart's natural pacemaker) is a medical device that uses electrical impulses, delivered by electrodes contacting the heart muscles, to regulate the beating of the heart. The electrodes may be covered by tubing or other material that includes a surface that may require endothelialization and grooves thereon. Earrings and other piercings may benefit from the topographical features, as well as any other implant, whether the implant is an organic, inorganic, mechanical, electrical, or biological device.

Although photolithography methodologies are discussed herein as a method of forming the noncontiguous pattern of topographical features, the present invention is not so limited. Any methodology to form the noncontiguous pattern of topographical features may be utilized, including photolithography, mechanical transfer, electrochemical machining, laser etching, electric discharge machining, and/or any other means of applying the pattern to a surface of the medical device. Generally, the present invention may comprise forming or providing a medical device having at least one surface and forming at least one noncontiguous pattern of topographical features in or on said surface.

Adding topographical or groove features to the surface of a stent has been shown to accelerate the migration rate of cells. However, topographical or groove features impart the greatest benefit when the topographical or groove features are placed parallel with fluid flow, and provide little to no benefit when the topographical or groove features are oriented perpendicular to the fluid flow. This perpendicular orientation can be problematic for continuous topographical or groove features, since the final shape or orientation of the features can vary depending on the condition, size, shape, and/or compliance of the blood vessel, lumen, or tissue where the device is implanted.

Figure 6A:
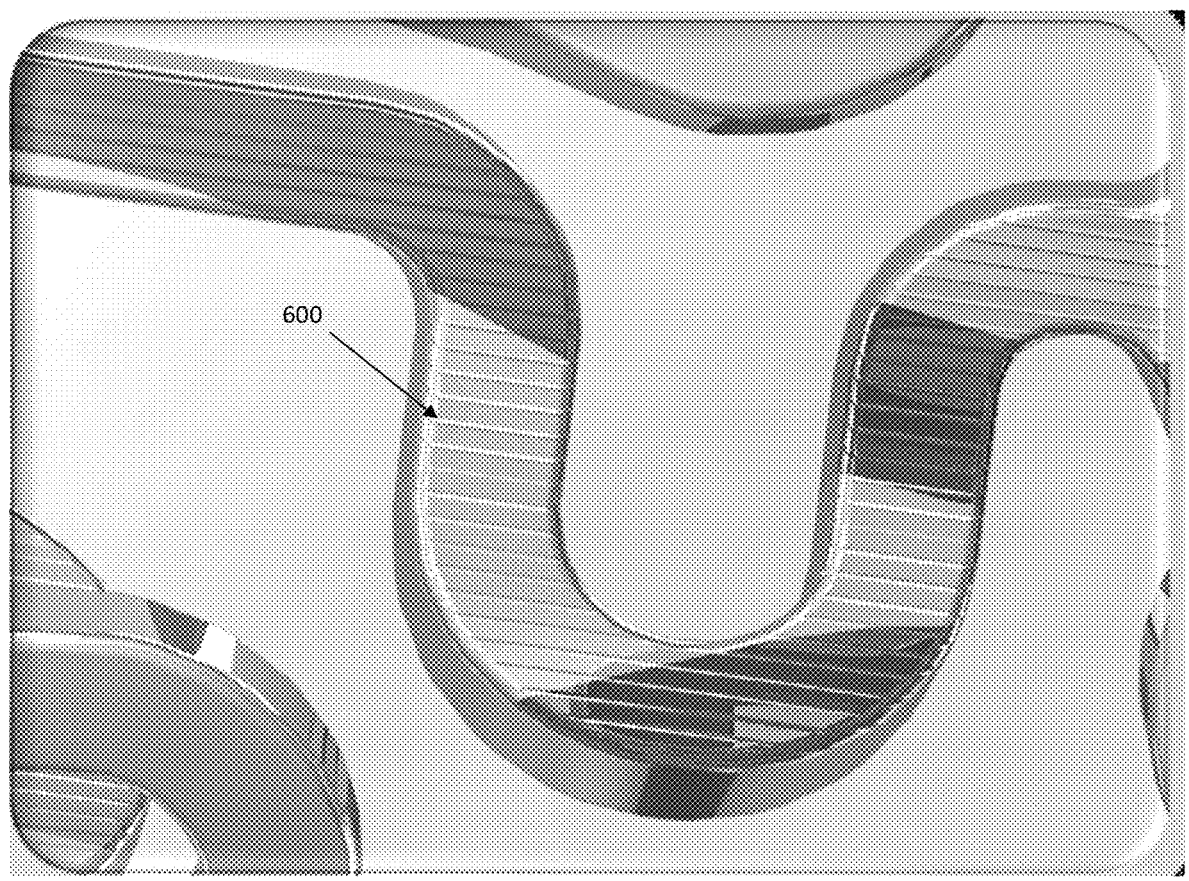
FIGS. 6a-6b is an illustration of a stent having a pattern of continuous grooves in an inner surface of the stent.
Figure 6B:
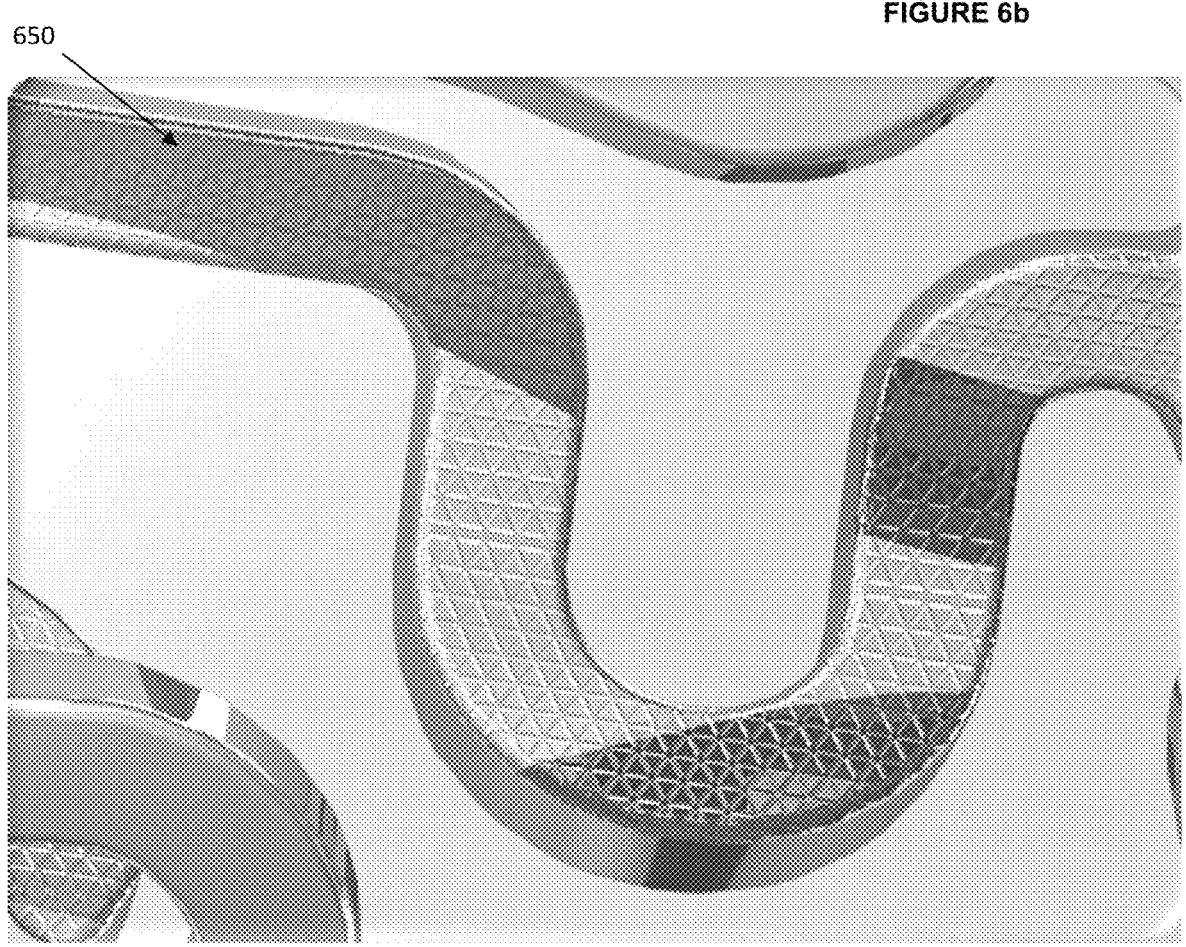

The device design itself may also not be well suited for continuous topographical or groove features. Some geometries do not allow for cell migration across all areas of the device, without the cells traveling over the vessel or lumen wall. One such example of a continuous groove feature can be seen in FIG. 6a. If evenly spaced, some topographical or groove features may only allow for a very small distance of travel, as seen in region 600 of FIG. 6a. Still further, a stent with a large expansion ratio can result in more grooves losing their proper orientation with blood flow. FIG. 6b illustrates a similar stent geometry to FIG. 6a, however a noncontiguous pattern of topographical features 650 is imparted to a surface of the stent. As can be seen, regardless of the orientation of the stent, cells may migrate across all areas of the stent, unlike with the continuous grooves in FIG. 6a.

Figure 5B:
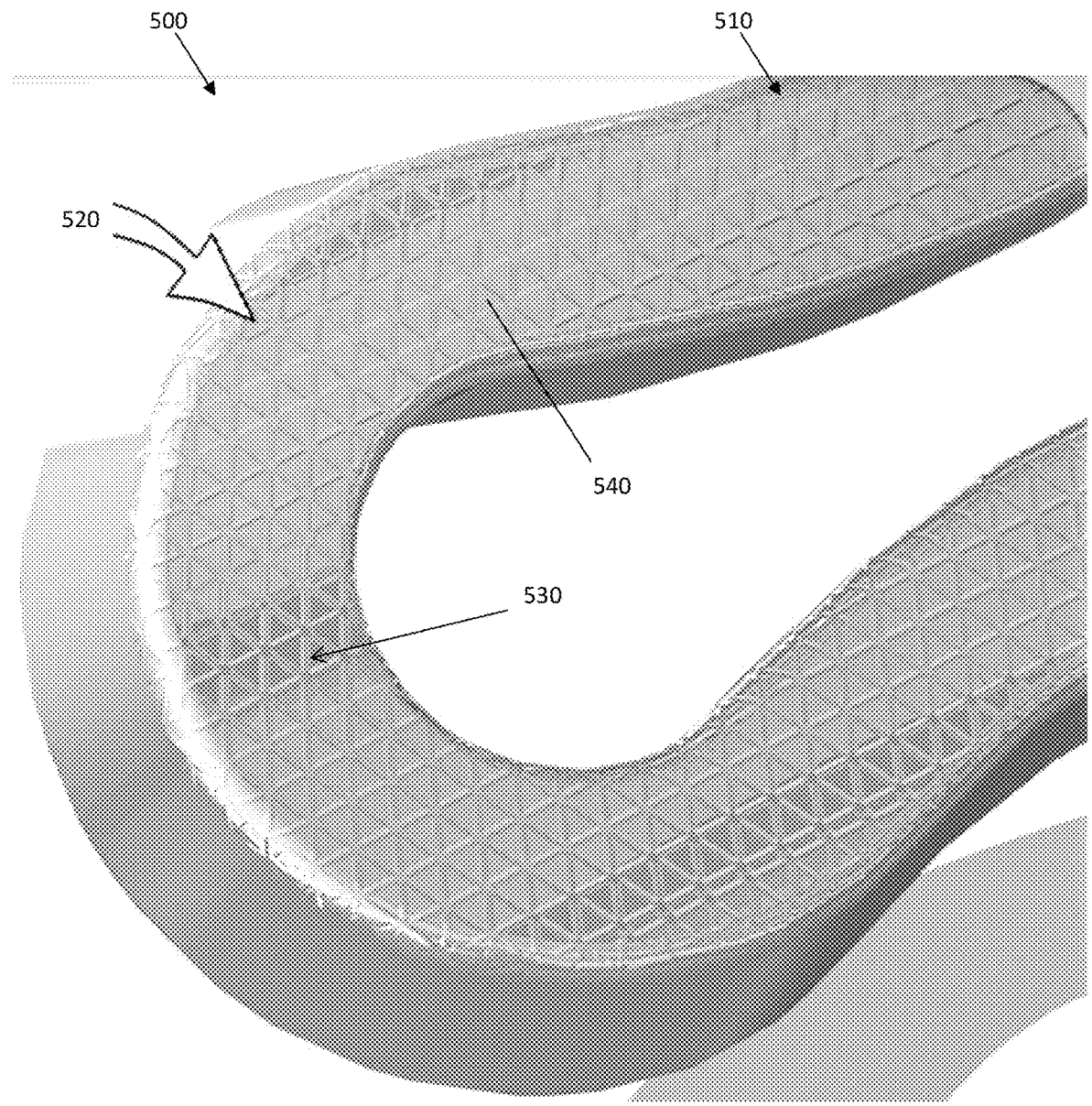

A noncontiguous topographical pattern 520 on at least one surface 510 of a medical device 500 allows for cell migration in more than one direction, as shown in FIGS. 5a-b. The noncontiguous pattern allows the cells to migrate in the direction of blood flow, regardless of the final positioning of the surfaces or structures of the medical device. In one embodiment, the noncontiguous topographical pattern 520 includes a plurality of grooves 530 forming a triangular shape 540 on the surface 510 of the device 500. The triangular shapes 540 alternate in facing one direction and then the opposite direction, as to form a row of alternating facing triangular shapes 540.

Figure 7A:
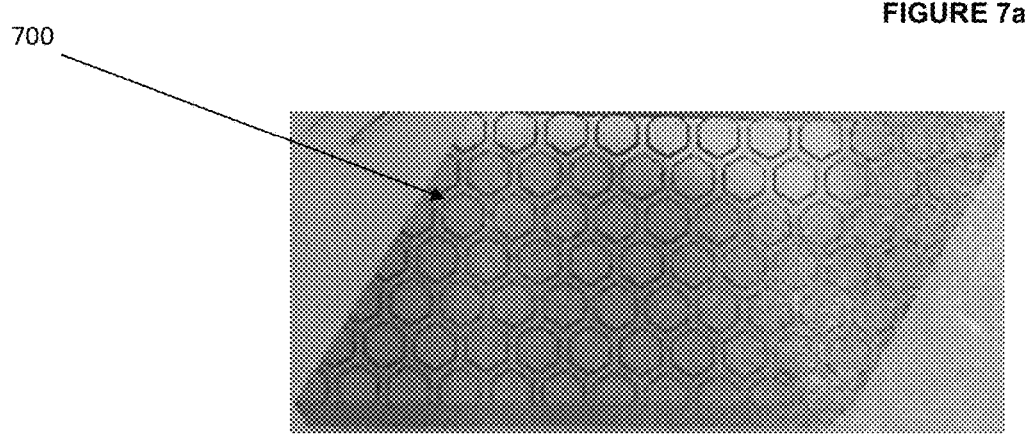
FIGS. 7a-7c are illustrations of different noncontiguous patterns of topographical features imparted in a surface of a medical device.
Figure 7B:
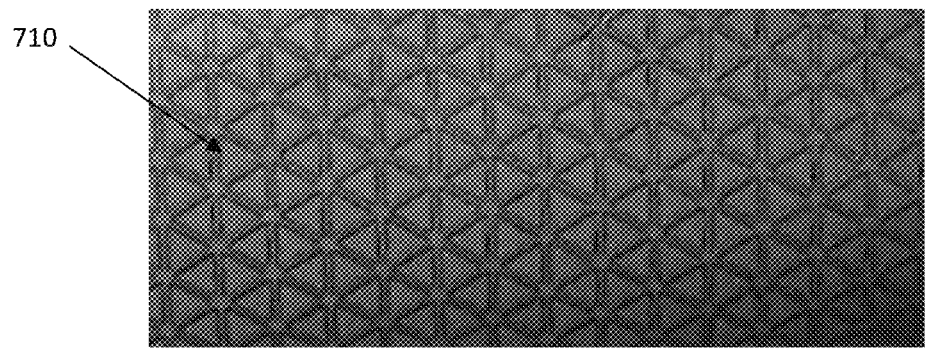
Figure 7C:
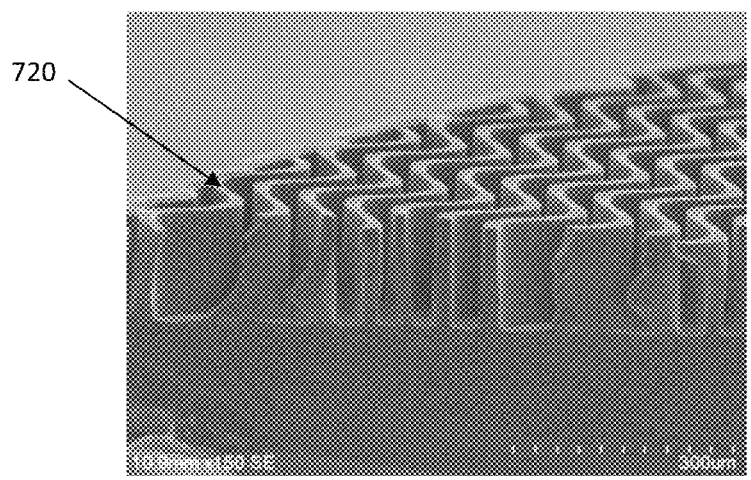
Figure 8A:
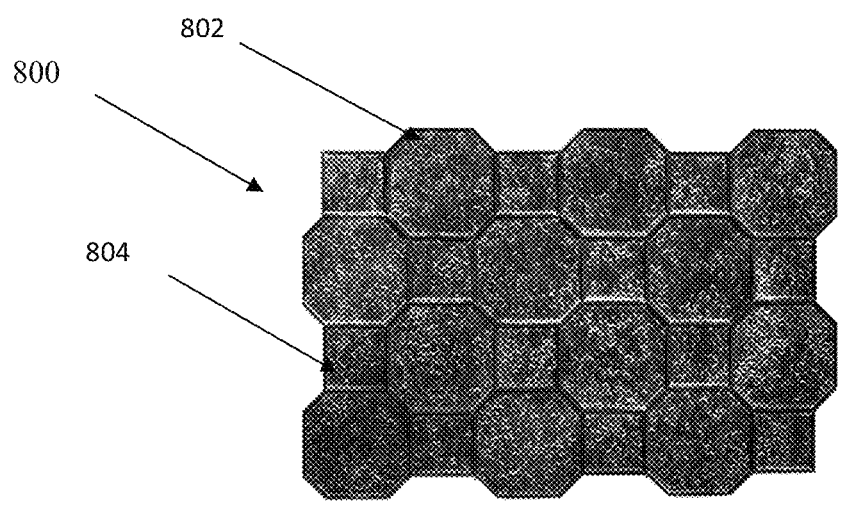
FIGS. 8a-8f are illustrations of different noncontiguous patterns of topographical features imparted in a surface of a medical device.
Figure 8B:
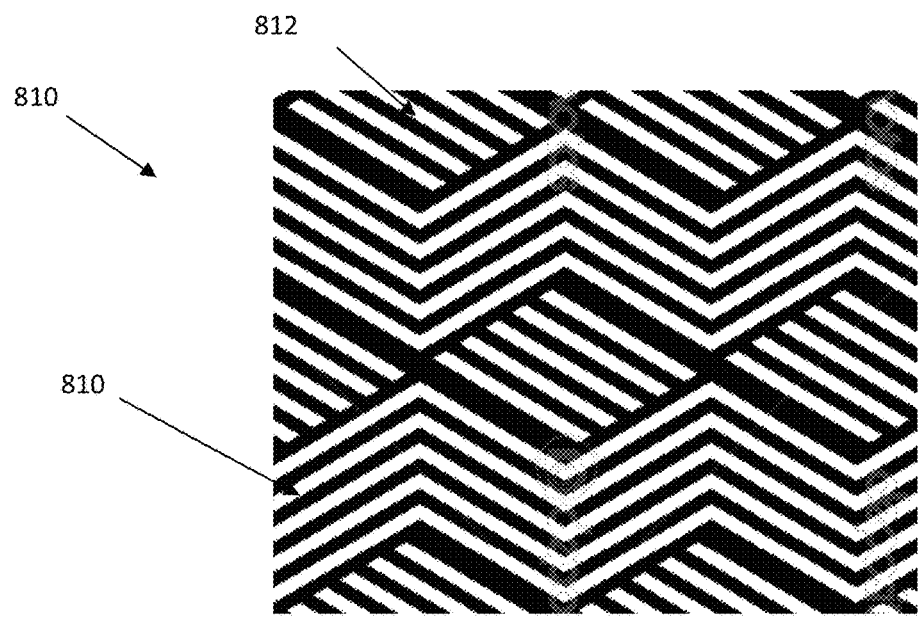
Figure 8C:
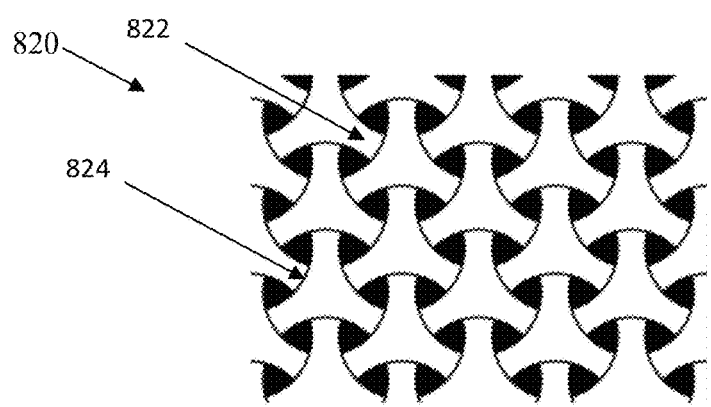
Figure 8D:
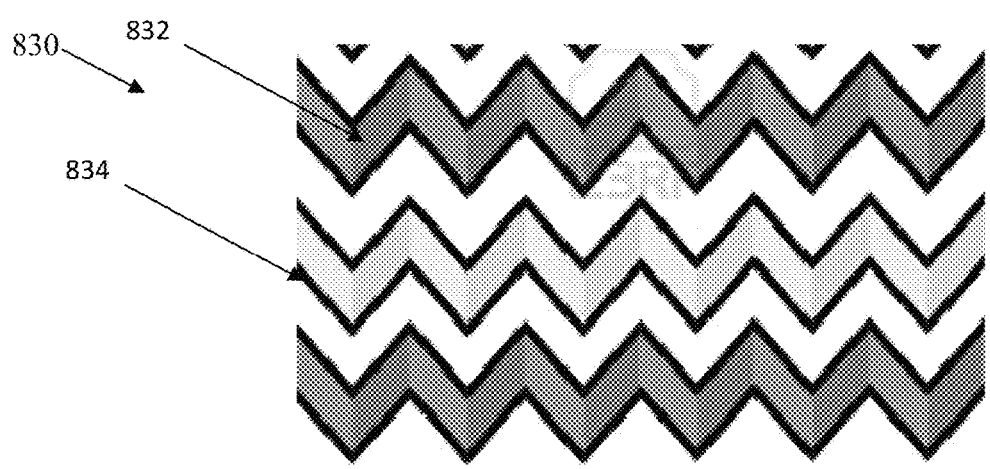
Figure 8E:
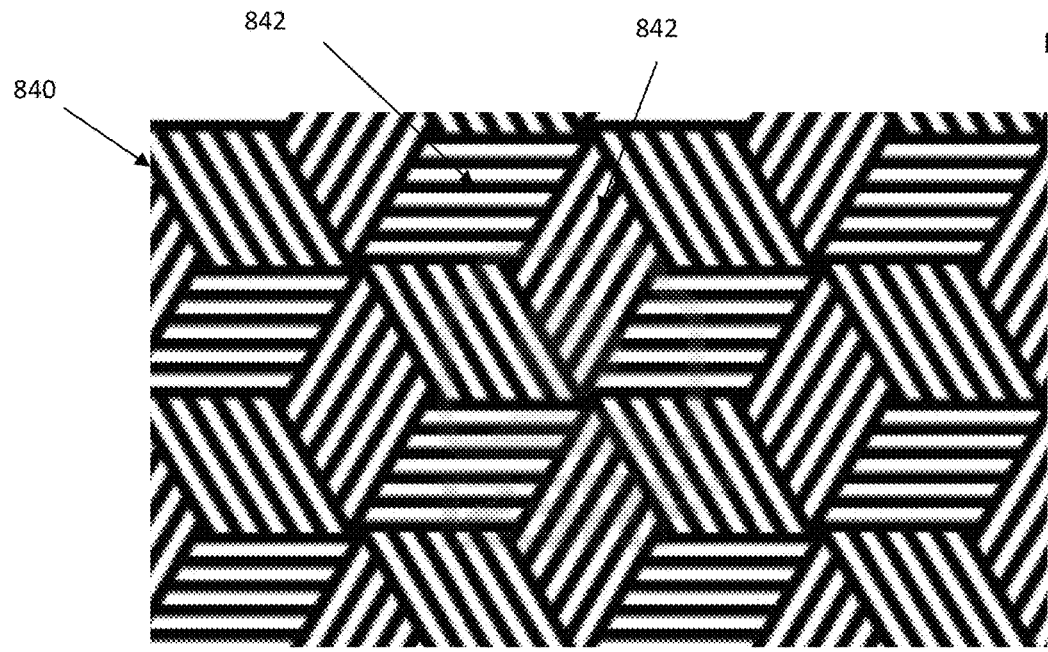
Figure 8F:
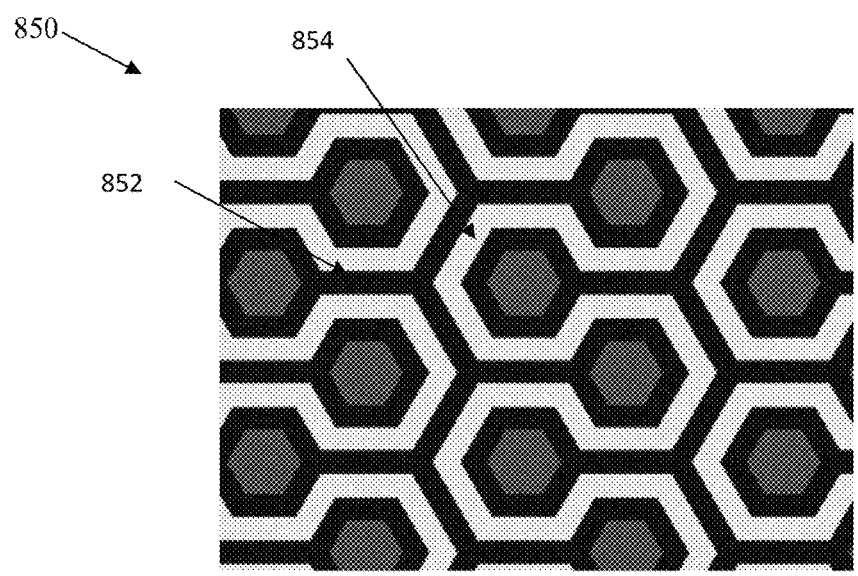

The pattern itself could be any noncontiguous shape that promotes a favorable cell response, as further discussed below in relation to FIGS. 7a-7b. The shapes could be of any size, number, height, or depth required to issue a proper cell response. The limit of the distance for the noncontiguous pattern may be across a particular length or depth. In one embodiment, the noncontiguous pattern includes a continuous groove for at least 0.1-5.0 microns in length, alternatively, at least 10.0 microns in length, alternatively, at least 1.0-100.0 microns in length. Then noncontiguous groove is placed at an angle thereafter, preferably between about 10-150 degrees, alternatively, between about 20-120 degrees, alternatively, between about 30-100 degrees. In one embodiment, the noncontiguous pattern may take place after 5-10 microns of groove length. In one embodiment, the noncontiguous pattern may be sinusoidal pattern 720 of curved lines, as shown in FIG. 7C. The sinusoidal pattern 720 of curved lines may have a specific wavelength and amplitude, may have a constant amplitude and wavelength, or may a discontinuous amplitude and wavelength that varies along the length of the groove. The wavelength and the amplitude of the sinusoidal pattern 720 may be at least 0.1-5.0 microns in length, alternatively, at least 10.0 microns in length, alternatively, at least 1.0-100.0 microns in length Alternatively, as shown in FIG. 8A, the noncontiguous shapes may include intermatched shaped pattern 800, such as alternating octagonal grooved features 802 displaced with square grooved features 804. Alternatively, the noncontiguous pattern may be alternating diagonal groove pattern with alternating diagonal groove 812 and 814 displaced at an angle, as shown in FIG. 8B. Alternatively, the noncontiguous pattern may be boomerang like shape 820 with three prongs 822 stemming from curved portions 824, wherein the end of each prong 820 abuts an adjacent curved portion 824, as shown in FIG. 8C. Alternatively, the noncontiguous pattern may be zig-zag like grooved feature 830, where the every fourth zig-zag groove 832 includes a depth greater than the previous grooved features 834, as shown in FIG. 8D. Alternatively, the noncontiguous pattern may include general hexagonal pattern 840 with at least three alternating diagonal groove features 842 disposed within each hexagonal pattern 830 and the plurality of diagonal groove features 842 terminate at an angle into a length of an adjacent diagonal groove feature 842, as shown in FIG. 8E. Alternatively, the noncontiguous pattern may include open hexagonal grooved features 850 whereby an inner hexagonal groove 852 encircles an outer hexagonal groove 854 about at least one point, and the inner hexagonal groove 852 may be a different width or depth than the outer hexagonal groove 854, as shown in FIG. 8F.

These features could be added to surfaces of articles other than stents. The term "stent" is used throughout this application to simplify the explanation, but is not intended to be a limiting description. As stated above, the inventive implantable devices may be intravascular stents, stent-grafts, grafts, heart valves, venous valves, filters, occlusion devices, catheters, sheaths, osteal implants, implantable contraceptives, implantable antitumor pellets or rods, shunts and patches, pacemakers, needles, temporary fixation rods, medical wires or medical tubes for any type of medical device, or other implantable medical devices, as will also be hereinafter described.

Using photolithography, mechanical machining, micromachining, laser machining, or other means to transfer the pattern, a pattern of multiple non-contiguous shapes can be produced in or on the surface of an implantable medical device to promote healing, by allowing for cell migration in the direction of blood flow regardless of alignment of the device after implantation. The noncontiguous pattern of topographical features may be created through photolithography, mechanical transfer, electrochemical machining, or any other means of applying the pattern to a surface of the device. These new techniques embodied in the present invention described herein provide the opportunity to apply not just grooved features, but any conceivable pattern of shapes.

Additionally, not only may these patterns be utilized for cell migration, but also to allow for cells to spread quickly to the sides once the path in the direction of blood flow is occupied by existing cells. This may be particularly useful for specific implantable medical devices, such as heart valves.

In still further embodiments, the noncontiguous pattern of topographical features can be used to promote other cell responses, such as demoting cell proliferation, pinning cells in place, thwarting tissue growth, enhancing osteoblast formation, and/or the like. Surface modification could include geometric features, charge distribution, alternative chemistry for the patterns, coatings on the patterns, oxides on the patterns, nitrides on the patterns, and the like.

Pattern Shape

The pattern itself could be any noncontiguous shape that promotes a favorable cell response. The shapes could be of any size, number, height, or depth required to issue a proper cell response. Illustrations of exemplary patterns are shown in FIGS. 7-8. FIG. 7A depicts a hexagonal noncontiguous pattern of topographical features 700. FIG. 7B depicts a triangular noncontiguous pattern of topographical features 800. FIG. 8 depicts an intermatched shaped pattern 800, such as alternating octagonal grooved features 802 displaced with square grooved features 8040.

Additionally, in further embodiments, the noncontiguous pattern of topographical features could be placed anywhere on a surface of the device, could be used on external surfaces of the device to prevent cell migration, or could be used for drug delivery. For example, considering a disposable device such as a needle used with an insulin pump, it may be advantageous to thwart tissue growth to ease removal of the temporary device. Other similar devices may include temporary fixation rods used for knee, shoulder, or elbow repair, and/or the like. Devices with a noncontiguous pattern of topographical features may also be useful for promoting healing at closure sites, or for bone mending (such as the breastplate after open heart surgery).

In some embodiments, multiple noncontiguous patterns of topographical features may be imparted to a single device, such as on different surfaces or different portions of a surface, to achieve different cell responses for different objectives. For example, considering a heart valve, a first noncontiguous pattern of topographical features could be incorporated in the anchoring portion of the heart valve and a second noncontiguous pattern of topographical features incorporated near the leaflets of the valve to prevent tissue growth on the leaflets.

With reference to FIG. 1, the method of creating a noncontiguous pattern of topographical features on a surface of a medical device 100 is illustrated. First, a medical device is provided 105. In a preferred embodiment, the medical device is metallic in nature, but need only be suitable for chemical machining. Photoresist is then applied to the device and treated appropriately to make the photoresist photosensitive 110. A positive or negative photoresist may be used. In a preferred embodiment, the photoresist is an electrodeposited positive photoresist (InterVi™ 3D-P Photoresist PEPR-2400) from MicroChem. Alternative photoresists are contemplated by and within the scope of this disclosure, including negative photoresist. By electrodepositing the photoresist, all surfaces of the device are easily coated with a uniform layer of resist, as compared to traditional photoresist application methods. It is important to attain sufficient control over coating thickness on especially the inner diameter of the stent. In alternative embodiments, the device may be coated with photoresist by dipping, spraying, spinning, electrodeposition, or any other typical means of applying photoresist. Once the device is coated, the device is mounted on a photomasked transparent apparatus 115. The method of creating the photomasked transparent apparatus is discussed further below, in relation to FIG. 3. In mounting the device on the photomasked apparatus, it is preferable to maintain intimate contact between the device and apparatus, to aid in pattern transfer. In one embodiment, an external force is applied to the device to obtain this intimate contact. In another embodiment, an interference fit between the apparatus and the device can be used to obtain the intimate contact. In embodiments where the device is nitinol-based, the interference fit may be obtained by shape memory. Once the device is mounted on the apparatus, the photoresist coating on the device is exposed to exposing radiation through the photomasked apparatus 120. In a preferred embodiment, the exposing radiation is an ultraviolet light source, though the light source could have any wavelength that is compatible with the particular photoresist utilized by the inventive method. One such source is a light guide or an internal 0.7 mm fiber with UV radiation provided by a 200 W Lesco SuperSpot Max-HP source. In an alternative embodiment, the exposing radiation may be atomic in nature. The exposing radiation may be transmitted through one edge of the apparatus, or transmitted by means of a fiber optic cable inserted within the apparatus below the photomask. If a fiber optic cable is used, either an end transmitting fiber optic cable may be translated within the apparatus to gain even exposures, or a bare (preferably frosted) fiber may be used to broadcast the exposing radiation from within the apparatus. After exposure, the now exposed device is removed from the apparatus 125. The exposed photoresist is then developed to reveal the noncontiguous pattern imparted by the photomask 130. In one embodiment, a rinse process may then be employed on the exposed photoresist to enhance pattern coverage and give rise to about 100% pattern coverage. Some metals may a rinse of warmed deionized water, while other metals may not require the rinse step. In the preferred embodiment, using a positive photoresist, developing exposes the base material of the device in the exposed portions of the photoresist through the use of appropriate chemicals. In the preferred embodiment, the appropriate chemicals are those recommended by the manufacturer of the photoresist, including InterVia™ 3D-P Developer, InterVia™ 3D-P Remover, InterVia™ 3D-P Solvent, and InterVia™ 3D-P TC. The exposed base material of the device may then be chemically machined to a desired depth 1350. The machining may be accomplished by wet or dry chemical etching or polishing, or by electrochemical machining. In one embodiment, the electrochemical methods are carried out in a phosphoric acid bath. Once the machining is complete, the remaining photoresist may be removed from the device 140, by appropriate means. Appropriate means may include chemical or mechanical removal of the remaining photoresist. The result is a medical device having a noncontiguous pattern of topographical features created on at least one surface of the device.

In a further embodiment, after the machining is complete, the patterning and machining process can be repeated using additional transparent apparatuses, having distinct photomask patterns, to achieve multiple-depth noncontiguous patterns of topographical features on the surface of the device. Alternatively, the patterning and machining process can be repeated to impart distinct noncontiguous patterns of topographical features to different portions or surfaces of the device, having the same or different depths, patterns, shapes, etc.

Figure 2:
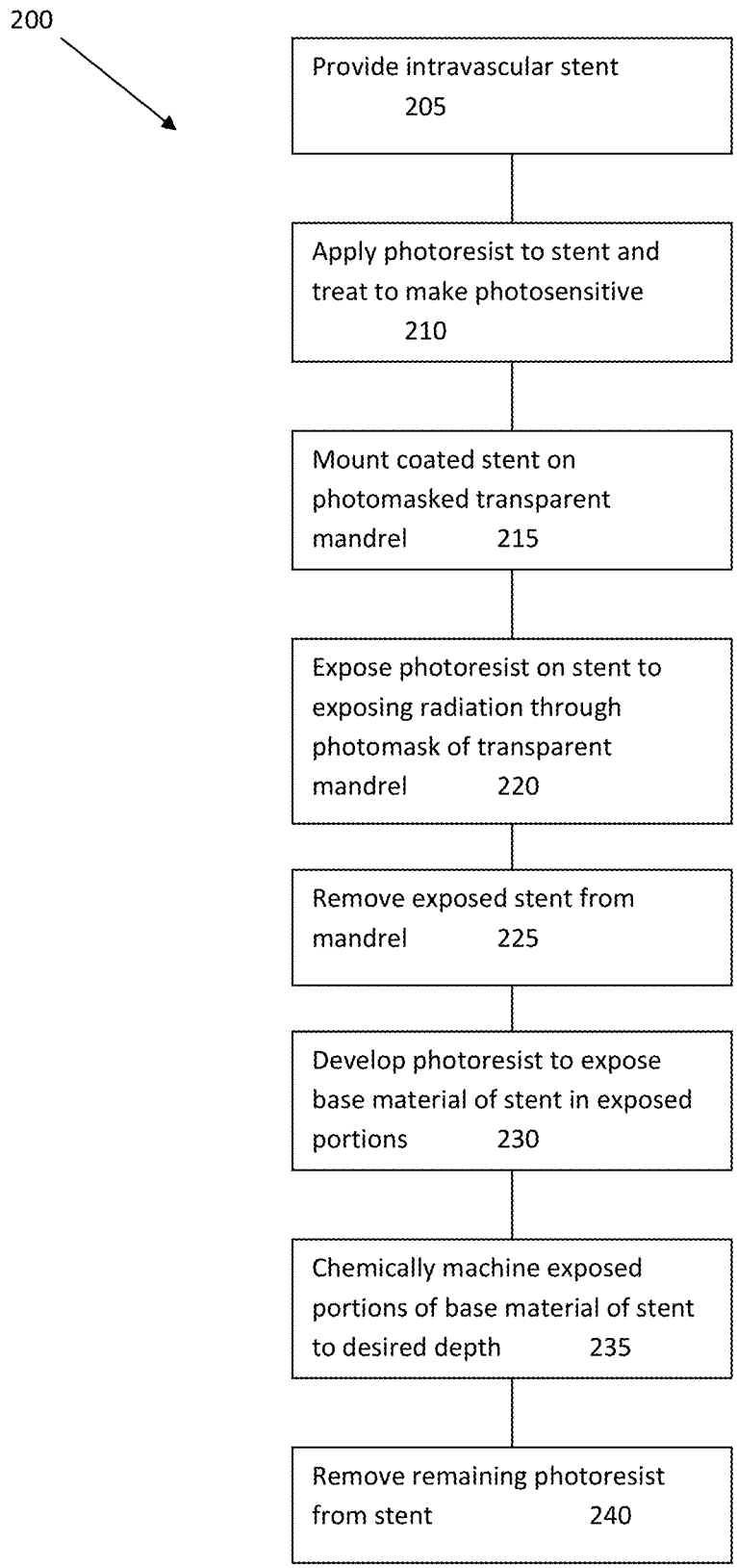
FIG. 2 is a block diagram illustrating a method of manufacturing an intravascular stent having at least one noncontiguous pattern of topographical features created in or on the inner surface thereof.

With reference to FIG. 2, the method of creating a noncontiguous pattern of topographical features on the inner diameter surface of an intravascular stent 200 is illustrated. First, an intravascular stent is provided 205. In a preferred embodiment, the intravascular stent is metallic in nature, but the material of the intravascular stent need only be suitable for chemical machining. Photoresist is then applied to the stent and treated appropriately to make the photoresist photosensitive 210. In a preferred embodiment, the photoresist is an electrodeposited positive photoresist (InterVia™ 3D-P Photoresist PEPR-2400) from MicroChem. Alternative photoresists are contemplated by and within the scope of this disclosure, including negative photoresist. If a negative photoresist is used, additional steps are required to expose the masked portions of the stent and then expose the remaining surfaces. By electrodepositing the photoresist, all surfaces of the stent are easily coated with a uniform layer of resist, as compared to traditional photoresist application methods. It is important to attain sufficient control over coating thickness on especially the inner diameter of the stent. In alternative embodiments, the stent may be coated with photoresist by dipping, spraying, spinning, electrodeposition, or any other typical means of applying photoresist. Once the stent is coated, the stent is mounted on a photomasked transparent mandrel 215. The method of creating the photomasked transparent mandrel is discussed further below, in relation to FIG. 4. In mounting the stent on the photomasked mandrel, it is preferable to maintain intimate contact between the stent and the mandrel, to aid in pattern transfer. In one embodiment, an external force is applied to the stent to obtain this intimate contact. In another embodiment, an interference fit between the mandrel and the stent can be used to obtain the intimate contact. In embodiments where the stent is nitinol-based, the interference fit may be obtained by shape memory. Once the stent is mounted on the mandrel, the photoresist coating on the stent is exposed to exposing radiation through the photomasked mandrel 220. In a preferred embodiment, the exposing radiation is an ultraviolet light source, though the light source could have any wavelength that is compatible with the particular photoresist utilized by the inventive method. One such source is a light guide or an internal 0.7 mm fiber with UV radiation provided by a 200 W Lesco SuperSpot Max-HP source. In an alternative embodiment, the exposing radiation may be atomic in nature. The exposing radiation may be transmitted through one end of the mandrel, or transmitted by means of a fiber optic cable inserted within the mandrel below the photomask. If a fiber optic cable is used, either an end transmitting fiber optic cable may be translated within the mandrel to gain even exposures, or a bare (preferably frosted) fiber may be used to broadcast the exposing radiation from within the mandrel. In one embodiment, certain light guide with high optical numerical aperture (NA) produces the pattern definition of the noncontiguous pattern. Light guides and fibers preferably emit optical radiation radially. The translated fibers may include a conical tip as the optical radiation exits at a perpendicular angle to the mask. The methods of illuminating the mask may include: 1) end lighting, which relies on internal reflection and transmission through the mask; 2) a diffuse internal light that broadcasts over an area large enough to expose the entire article (or multiple articles) without having to move the light relative to the mask; and 3) an end lit internal fiber that is translated inside the mask to expose the article one section at a time in a continuous manner. The third method allows for very long lengths to be exposed. In addition, the exposure can be varied or interrupted, if desired. The second method can also work using translation to expose longer length articles.

After exposure, the now exposed stent is removed from the mandrel 225. The exposed photoresist is then developed to reveal the noncontiguous pattern imparted by the photomask 230. In the preferred embodiment, using a positive photoresist, developing exposes the base material of the stent in the exposed portions of the photoresist through the use of appropriate chemicals. In the preferred embodiment, the appropriate chemicals are those recommended by the manufacturer of the photoresist, including InterVia™ 3D-P Developer, InterVia™ 3D-P Remover, InterVia™ 3D-P Solvent, and InterVia™ 3D-P TC. The exposed base material of the stent may then be chemically machined to a desired depth 235. The machining may be accomplished by wet or dry chemical etching or polishing, or by electrochemical machining. In one embodiment, the electrochemical methods are carried out in a phosphoric acid bath. Once the machining is complete, the remaining photoresist may be removed from the stent 240, by appropriate means. Appropriate means may include chemical or mechanical removal of the remaining photoresist. The result is an intravascular stent having a noncontiguous pattern of topographical features created on an inner diameter surface of the stent.

Figure 3:
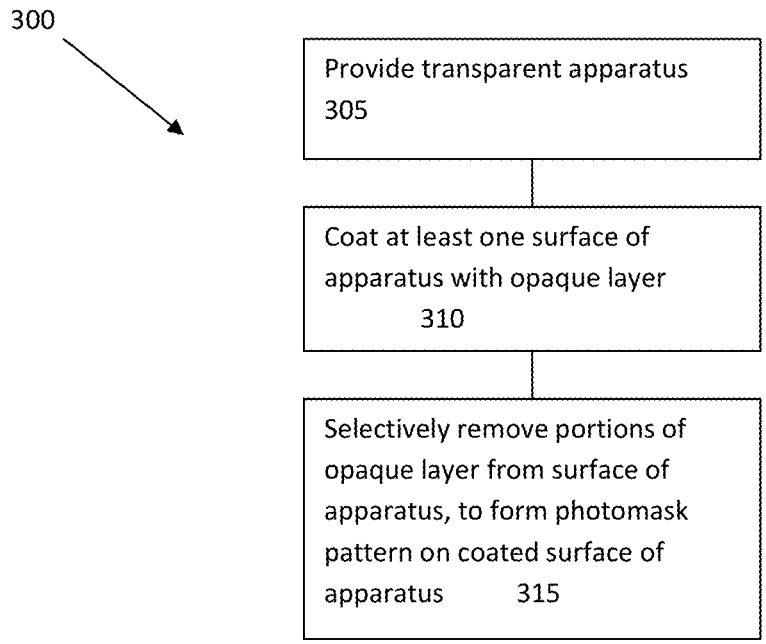
FIG. 3 is a block diagram illustrating a method of manufacturing a transparent apparatus having a surface adapted to mount a medical device thereupon, so as to impart a photomask pattern to a surface of the medical device.

With reference to FIG. 3, the method of manufacturing a photomasked transparent apparatus 3000 is illustrated. First, a transparent apparatus is provided 305. In a preferred embodiment, the transparent apparatus is comprised of quartz, glass, or any other material capable of transmitting an exposing radiation through a photomask onto a photoresist coated medical device. The transparent apparatus has at least one surface adapted to mount a medical device thereupon. The at least one surface of the transparent apparatus is then coated with an opaque layer 310. In one embodiment, the opaque layer is a thin wall material on the top or bottom of the at least one surface. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. Once coated, portions of the opaque layer may be selectively removed from the transparent apparatus by appropriate means 315, so as to form a photomask pattern on the surface of the apparatus. The appropriate means may include laser ablation, mechanical means, photolithography, etching, or engraving, and/or the like. With portions of the opaque layer removed, an exposing radiation is able to be transmitted through the now photomasked surface of the transparent apparatus.

Figure 4:
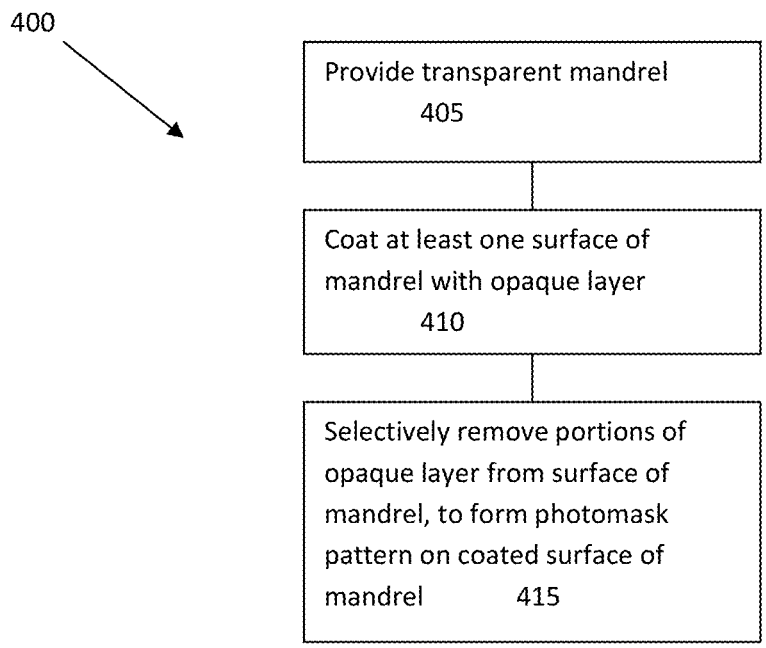
FIG. 4 is a block diagram illustrating a method of manufacturing a transparent mandrel for mounting an intravascular stent thereon, so as to impart a photomask pattern to the inner surface of the stent.

With reference to FIG. 4, the method of manufacturing a photomasked transparent apparatus 400 is illustrated. First, a transparent mandrel is provided 405. In a preferred embodiment, the transparent mandrel is comprised of quartz, glass, or any other material capable of transmitting an exposing radiation through a photomask onto a photoresist coated intravascular stent. In one embodiment, the mandrel is a cylindrical tube or rod. In alternative embodiments, the mandrel may be tapered, have an elliptical cross section, or have a polygonal cross section. The transparent mandrel has at least one surface adapted to mount an intravascular stent thereupon. In one embodiment, the mandrel has at least one open end, within which a fiber optic cable may be inserted for transmittal of the exposing radiation from within the mandrel through a photomask on the exterior of the mandrel. The at least one surface of the transparent mandrel is then coated with an opaque layer 410. In one embodiment, the opaque layer is a thin wall tube disposed against the inner or outer surface of the cylindrical mandrel. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. In the preferred embodiment, a metallic coating is deposited by physical vapor deposition on the outer surface of a cylindrical quart tube. Once coated, portions of the opaque layer may be selectively removed from the transparent mandrel by appropriate means 415, so as to form a photomask pattern on the surface of the mandrel. The appropriate means may include laser ablation, mechanical means, photolithography, etching, or engraving, and/or the like. In the preferred embodiment, the opaque layer is removed by laser ablation, utilizing a femtosecond laser cutting system. With portions of the opaque layer removed, an exposing radiation is able to be transmitted through the now photomasked surface of the transparent mandrel. Another method of producing the transparent mandrel is through the use of photolithography and chemical etch processes, which includes a photosensitive polymer coated on the mandrel and UV is applied selectively (e-beam or UV projection method).

Figure 9:
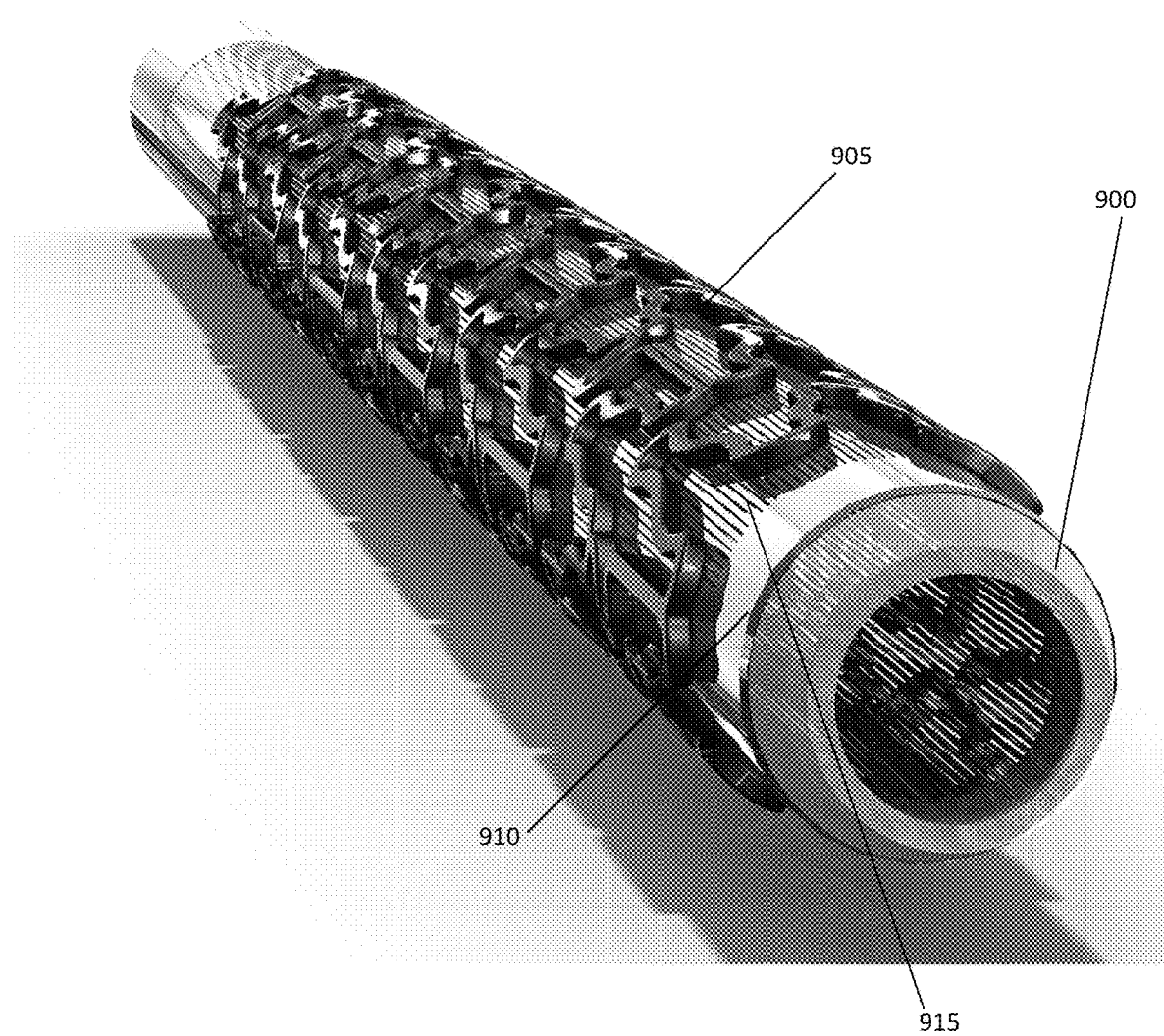
FIG. 9 is an illustration of one embodiment of the transparent mandrel of the present invention, having a photoresist coated stent mounted thereupon.

With reference to FIG. 9, one embodiment of the photomasked transparent mandrel having a photoresist coated stent is depicted. The transparent mandrel 900 is has a photoresist coated intravascular stent 905 mounted on the outer surface of the mandrel. The outer surface of the mandrel is coated with an opaque layer 910. Portions of the opaque layer 910 have been selectively removed to form a mask pattern, the mask pattern comprising openings 915 where the opaque layer has been removed.

In another embodiment of the present invention, the machined pattern may be used to enhance bone formation by enhancing osteoblast production for devices such as, but without limitation to, orthopedic or dental devices.

Figure 10A:
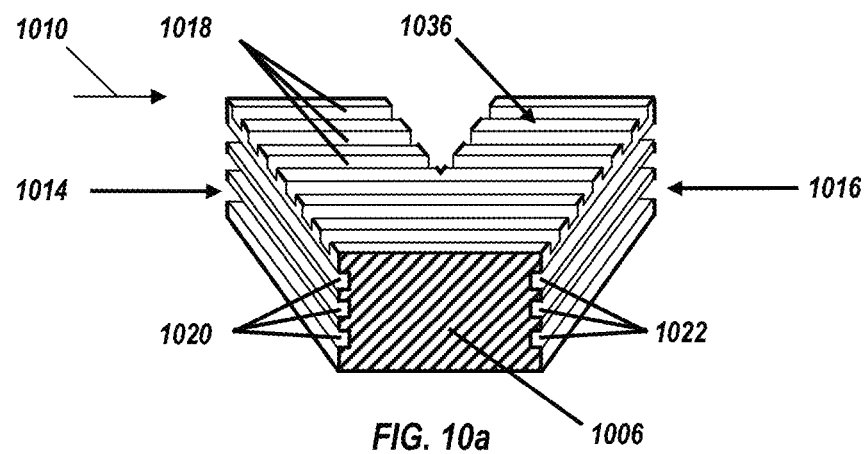
FIG. 10a is an illustration of one embodiment of an implantable medical device having surfaces imparted with topographical features.

Referring to FIG. 10A, a structural member 1006 includes a luminal surface 1036 as well as a leading edge 1014 and a trailing edge 1016 relative to the direction 1010 of blood flow. Any or all of the luminal surface 1036, the leading edge 1014, and the trailing edge 1016 may include topographical features disposed therein or thereon. For example, in one embodiment, the topographical features of luminal surface 1036 may be grooves 1018 disposed therein, and is noncontiguous by virtue of the edge of the structural member. The grooves 1018 may be oriented in any direction relative to the direction 1010 of blood flow; however, orientation of the grooves 1018 parallel to the direction 1010 of blood flow, as illustrated in FIG. 10A, exposes EC within the grooves 1018 to shear stress caused by the blood flow. As noted hereinabove, such exposure of EC to shear stress increases the rate of migration of the EC.

The leading edge 1014 of the structural member 1006, in one embodiment, may have topographical features such grooves 1020 disposed therein or thereon. The grooves 1020 may be oriented in any direction relative to the direction 1010 of blood flow and is noncontiguous by virtue of the edge of the structural member. In one embodiment as illustrated in FIG. 10A, the grooves 1020 are oriented such that a component of blood flow along the leading edge 1014 exposes EC within the grooves 1020 to shear stress caused by the blood flow. Similarly, the trailing edge 1016 of the structural member 1006, in one embodiment, may have topographical features such as grooves 1022 disposed therein or thereon. The grooves 1022 may be oriented in any direction relative to the direction 1010 of blood flow. In one embodiment as illustrated in FIG. 10A, the grooves 1022 are oriented such that a component of blood flow along the trailing edge 1016 exposes EC within the grooves 1022 to shear stress caused by the blood flow.

It should be noted that the topographical features on one or more of the surfaces 1036, 1014, 1016, may take any of a variety of forms, and are not limited to the grooves discussed above. For example, any or all of the grooves 1018, 1020, 1022 illustrated in FIG. 10A may alternatively be dots, divots, pores, holes, complex geometries, and/or the like.

Any of the geometrically functional features or recesses may also be included in the trailing edge, leading edge, or surface regions to enhance the endothelial migration and attachment to such surfaces.

An implantable device may include problematic surfaces that may be resistant to endothelialization or may otherwise be relatively slow to endothelialize. The problematic surfaces may be disadvantaged for cell adhesion because of, for example, hemodynamic reasons such as disruption via turbulence or low shear stress (which may occur in thick stents, for example, greater than about 100 µm) or chemical reasons such as anti-mitotic and/or anti-inflammatory drugs. The problematic surfaces could be, for example, stent bridges disposed at various angles against the blood flow.

Figure 10B:
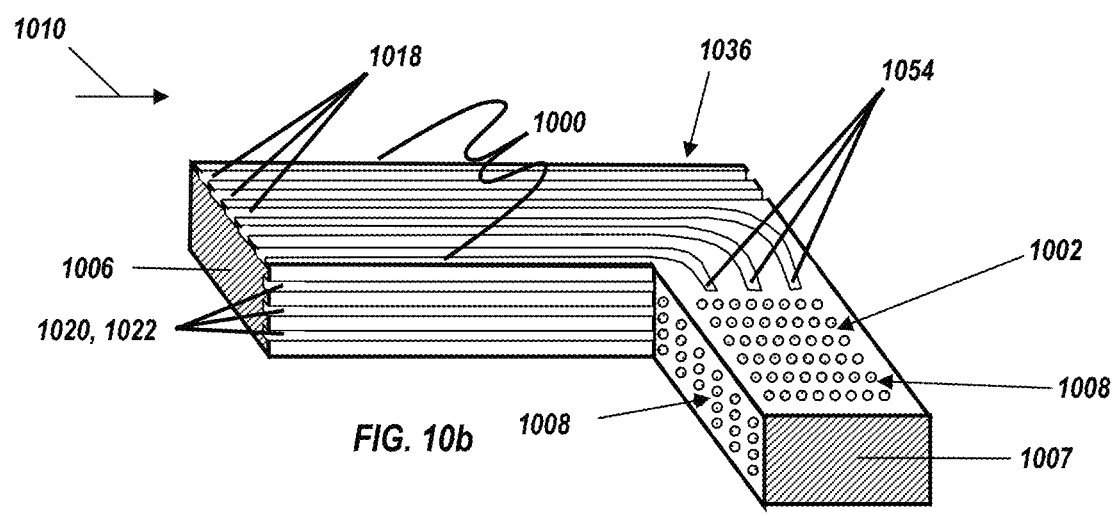
FIG. 10b is an illustration of one embodiment of an implantable medical device having surfaces imparted with topographical features, wherein the features include directional grooves and dots/pins.

Referring to FIG. 10b, it is contemplated that a combination of properly oriented grooves may facilitate EC migration to the problematic surfaces and/or promote cell stability thereon. For example, in one embodiment, a main highway 1000 of the grooves 1018 may be disposed in the luminal surface 1036 of the structural member 1006 and oriented generally parallel to the direction 1010 of blood flow, as illustrated in FIG. 10b. The main highway 1000 could provide an abundance of migrating EC, which could be diverted therefrom to a problematic surface, for example, a surface 1002 on a transversely disposed structural member 1007 of the implantable device. For example, the main highway 1000 may be diverted to groove endpoints 1054 on the transversely disposed structural member 1007 of the implantable device.

It is further contemplated that diversion of migrating EC from the main highway 1000 could be applied to surfaces having a specific function, and is noncontiguous by virtue of the diversion, which may or may not otherwise be conducive to EC migration. In some embodiments, the machined pattern may include features which pin or demote cell proliferation, so as to stop cell proliferation in a particular location. These patterns may be used to steer cells to control a directionality of healing response. In some embodiments, and without limitation, these features may be pores, holes, divots, and/or the like. FIG. 10b illustrates one embodiment of a surface with directional and pinning topographical features created thereupon. For example, referring to FIG. 10B, the structural member 1007 may include surfaces including a plurality of pores 1008 as might be found, for example, in a drug eluting stent. The plurality of pores may act to pin cell proliferation in the location of the pores 1008, and demote proliferation beyond the location of pores 1008.

In another embodiment of the present invention, the machined pattern may include features which pin or demote cell proliferation. These patterns may be used to steer cells to control a directionality of healing response. FIG. 10b illustrates one embodiment of a surface with directional topographical features created thereupon.

In one embodiment, a first pattern may be applied to a first surface of a dental implant, and a second pattern may be applied to a second surface of the dental implant. The first surface may serve to promote adhesion and healing of the implant in the bony part of the jaw, while the second surface may serve to stop proliferation of bone into the gum line.

Additional applications where it may be advantageous to demote healing include, without limitation, temporary implants such as a vena cava filter or an insulin pump needle.

In any embodiment of the present invention, an existing medical device, stent, or other article may be utilized. Through the use of an existing structure, it is likely that the regulatory path may be minimized.

Particular, non-limiting examples of medical devices that may be worked upon by the inventive method disclosed herein include dental implants, hip implants, and valves. Other devices may also be worked upon, as previously discussed above.

Figure 11A:
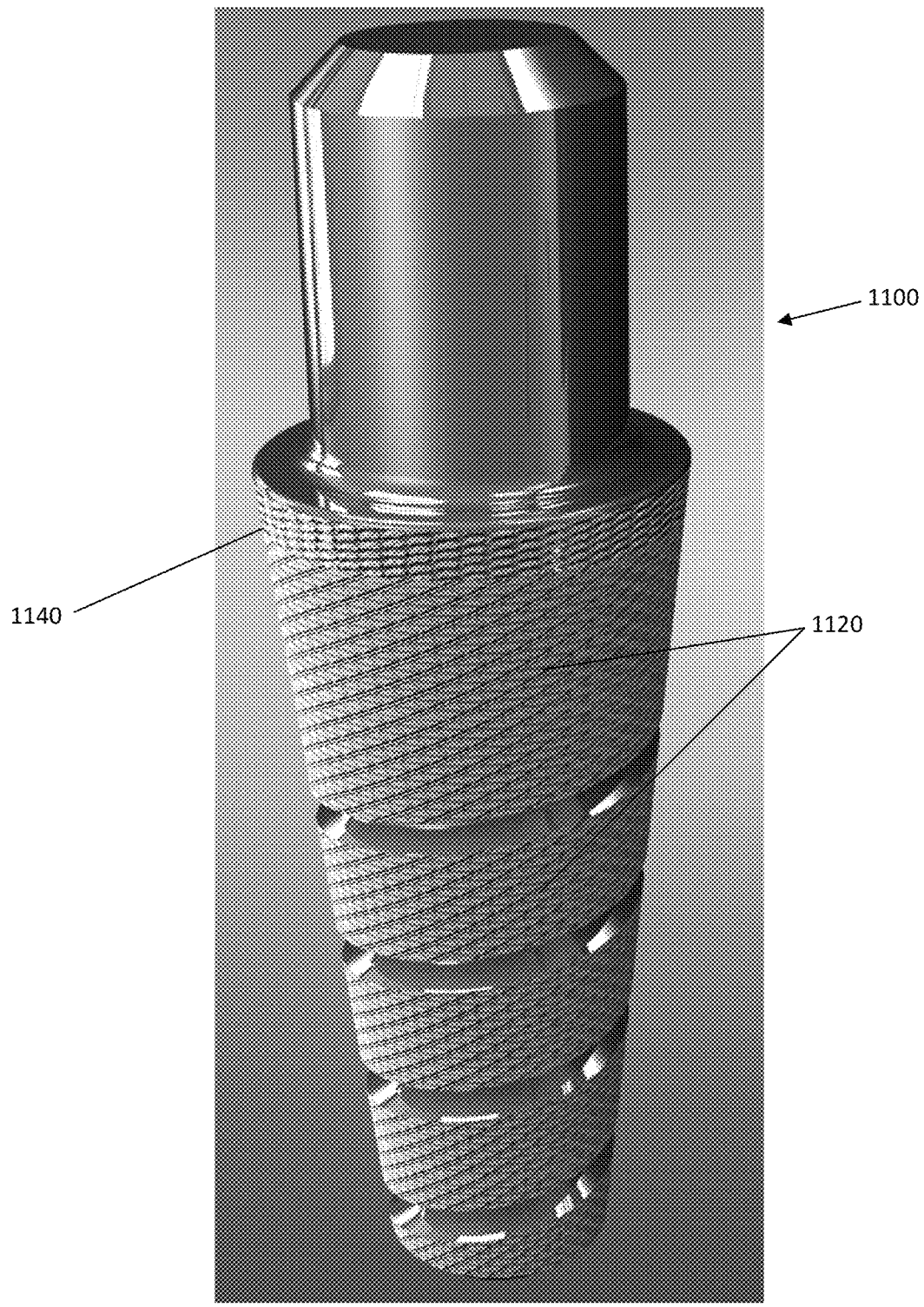
FIG. 11a is an illustration of a dental implant having topographical features.
Figure 11B:
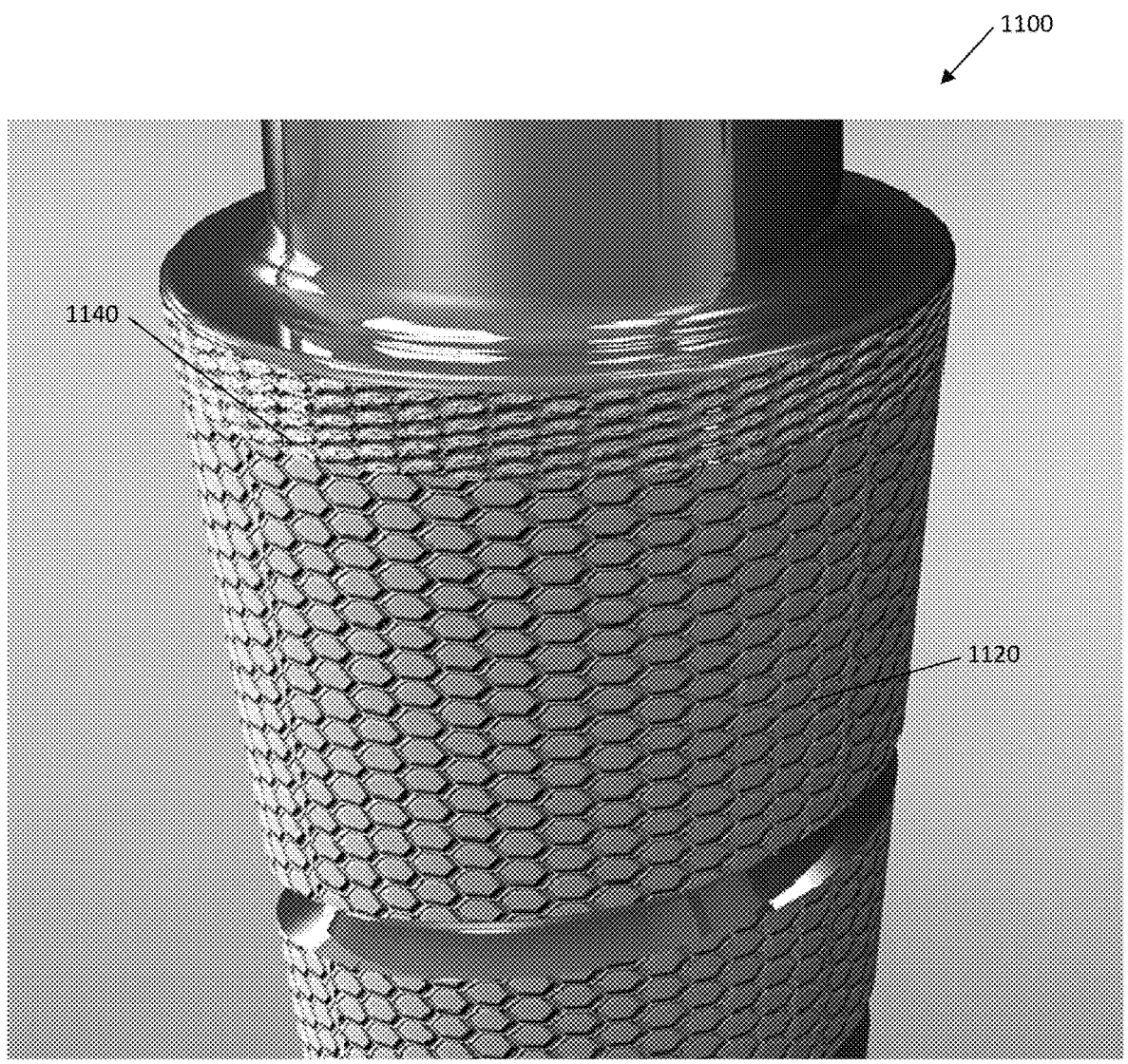

FIG. 11a depicts one embodiment of a textured dental implant 1100 having topographical features created thereupon. The dental implant 1100 has a portion imparted with a noncontiguous texture 1120 to promote bone growth in the jaw bone and a portion imparted with a dotted texture 1140 to pin the cells so they don't proliferate into the gums. In the depicted embodiment, the noncontiguous texture is alternating triangular grooved features that run along the length of the implant 1100, to provide directional migration of cells and thereby promote bone growth along and into the portion of the implant 1100 that is installed into the jaw bone of a patient. The portion of the implant 1100 having a dotted texture 1140 serves to halt the proliferation of cell growth such that the bone growth does not continue into the gums of the patient. The ideal texture for the bone growth may be a crosshatch to add an anchoring effect to the dental implant 1100. FIG. 11b is an enlarged view of the noncontiguous portion 1120 having displaced hexagonal grooved features and dotted portion 1140 of the dental implant 1100. In alternative embodiments, the features of the grooved portion 1120 may have different arrangements and/or noncontiguous shapes, such as noncontiguous grooves that run diagonally, noncontiguous grooves that run helically, complex geometries that promote bone growth along the length of the implant, features having multiple depths, and/or the like. The portion of the implant 1100 having a dotted texture 1140 may comprise divots, pores, holes, wells, and/or the like, serving to pin cells in place and thereby demote cell proliferation beyond the dotted portion 1140. In alternative embodiments, the features of the dotted portion 1140 may have different arrangements and/or shapes, or the portion may have greater or lesser width or height.

Figure 12A:
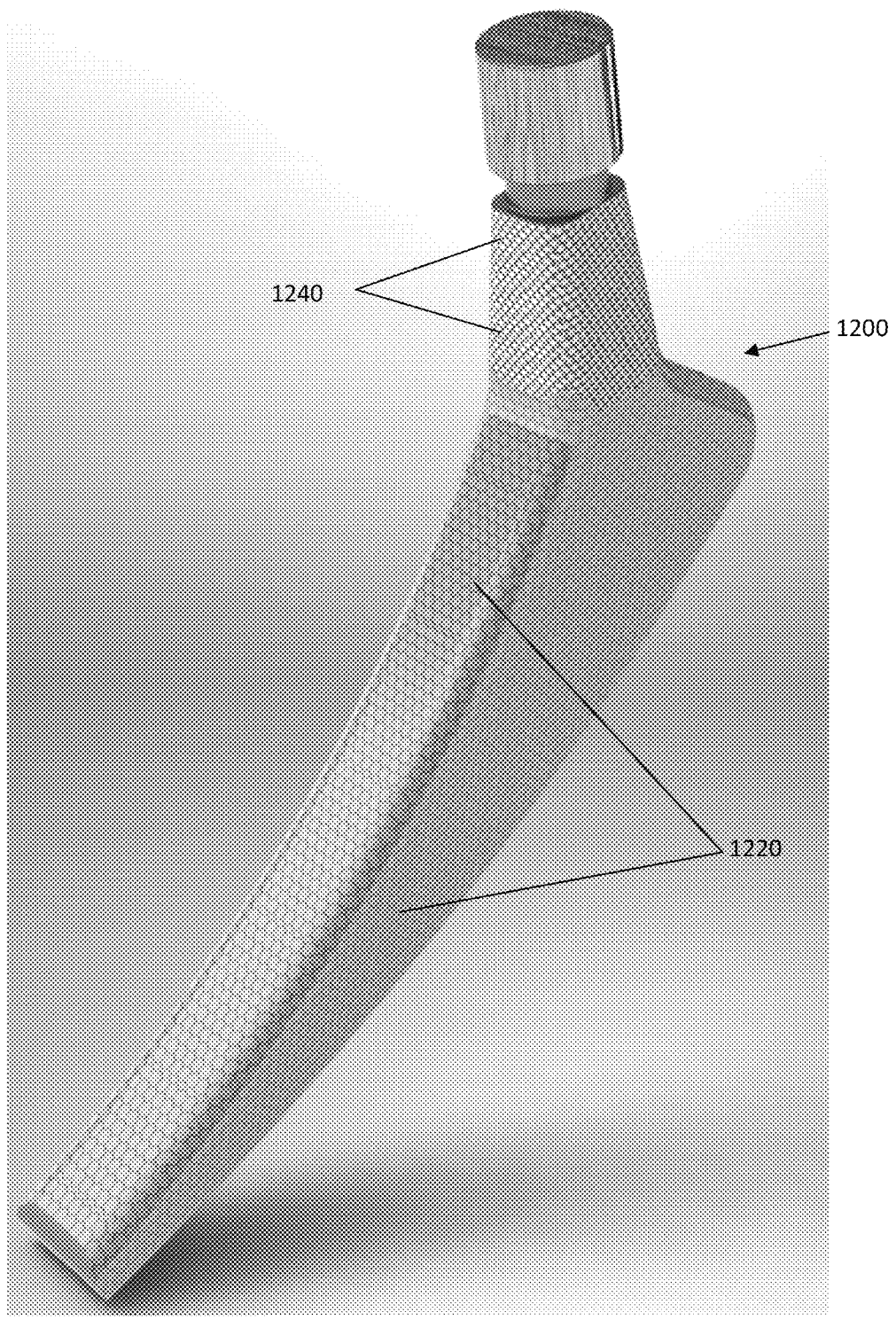
FIG. 12a is an illustration of a hip implant having topographical features.
Figure 12B:
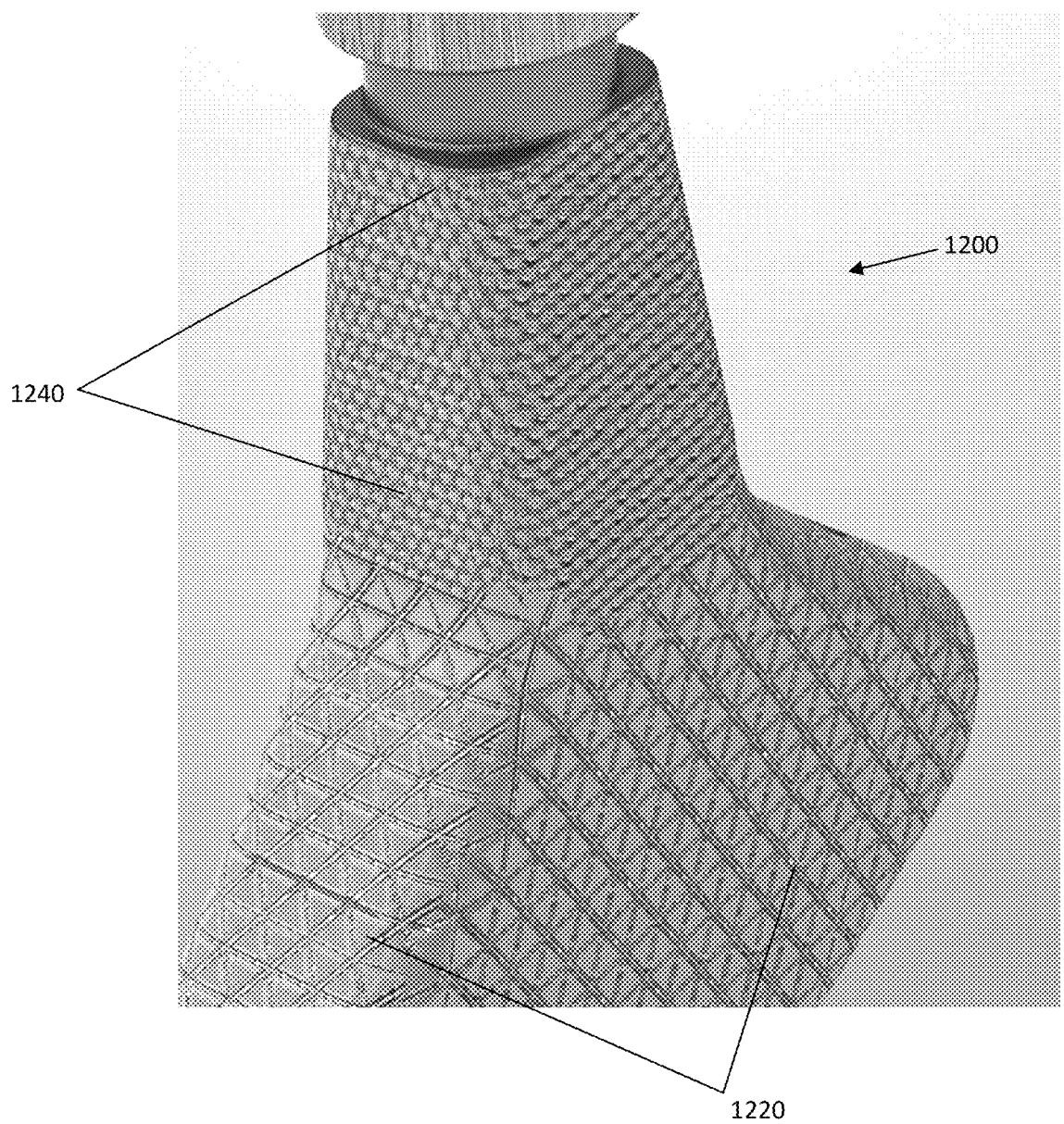
Figure 12C:
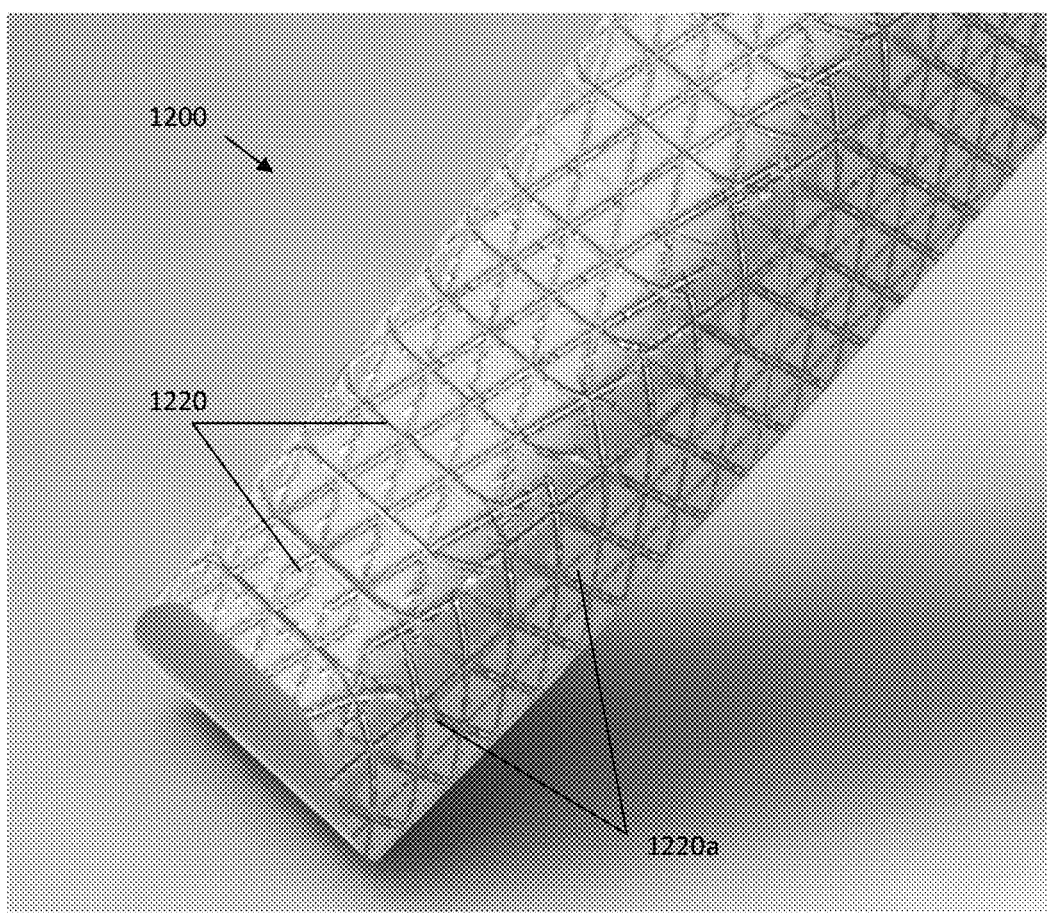

FIG. 12a depicts one embodiment of a textured hip implant 1200 having topographical features created thereupon. The hip implant 1200 has a portion imparted with a noncontiguous grooved texture 1220 to promote bone growth and a portion imparted with a dotted texture 1240 to pin the cells so they don't proliferate beyond the dotted portion. In the depicted embodiment, the grooves are an alternating hexagonal pattern that run along the length of the implant 1200, to provide multi-directional migration of cells and thereby promote bone growth along and into the portion of the implant 1200 that is installed into the bone of a patient. The portion of the implant 1200 having a dotted texture 1240 serves to halt the proliferation of cell growth such that the bone growth does not continue into the joint of the patient. The ideal texture for the bone growth may be a crosshatch to add an anchoring effect to the hip implant 1200. FIG. 12b is an enlarged view of the grooved portion 1220 that includes an noncontiguous triangular features and dotted portion 1240 of the hip implant 1200. In alternative embodiments, the features of the noncontiguous grooved portion 1220 may have different arrangements and/or shapes, such as noncontiguous grooves that run diagonally, noncontiguous grooves that run spirally, complex geometries of features that promote bone growth along the length of the implant, features having multiple depths, and/or the like. The portion of the implant 1200 having a dotted texture 1240 may comprise divots, pores, holes, wells, and/or the like, serving to pin cells in place and thereby demote cell proliferation beyond the dotted portion 1240. In alternative embodiments, the features of the dotted portion 1240 may have different arrangements and/or shapes, or the portion may have greater or lesser width or height. FIG. 12C shows the noncontiguous grooved portion 1220 on the distal portion including a first direction of the triangular grooves and a second direction of the triangular grooves 1220a in direction generally at an angle to the first direction of the grooves on the side of the implant.

Figure 13A:
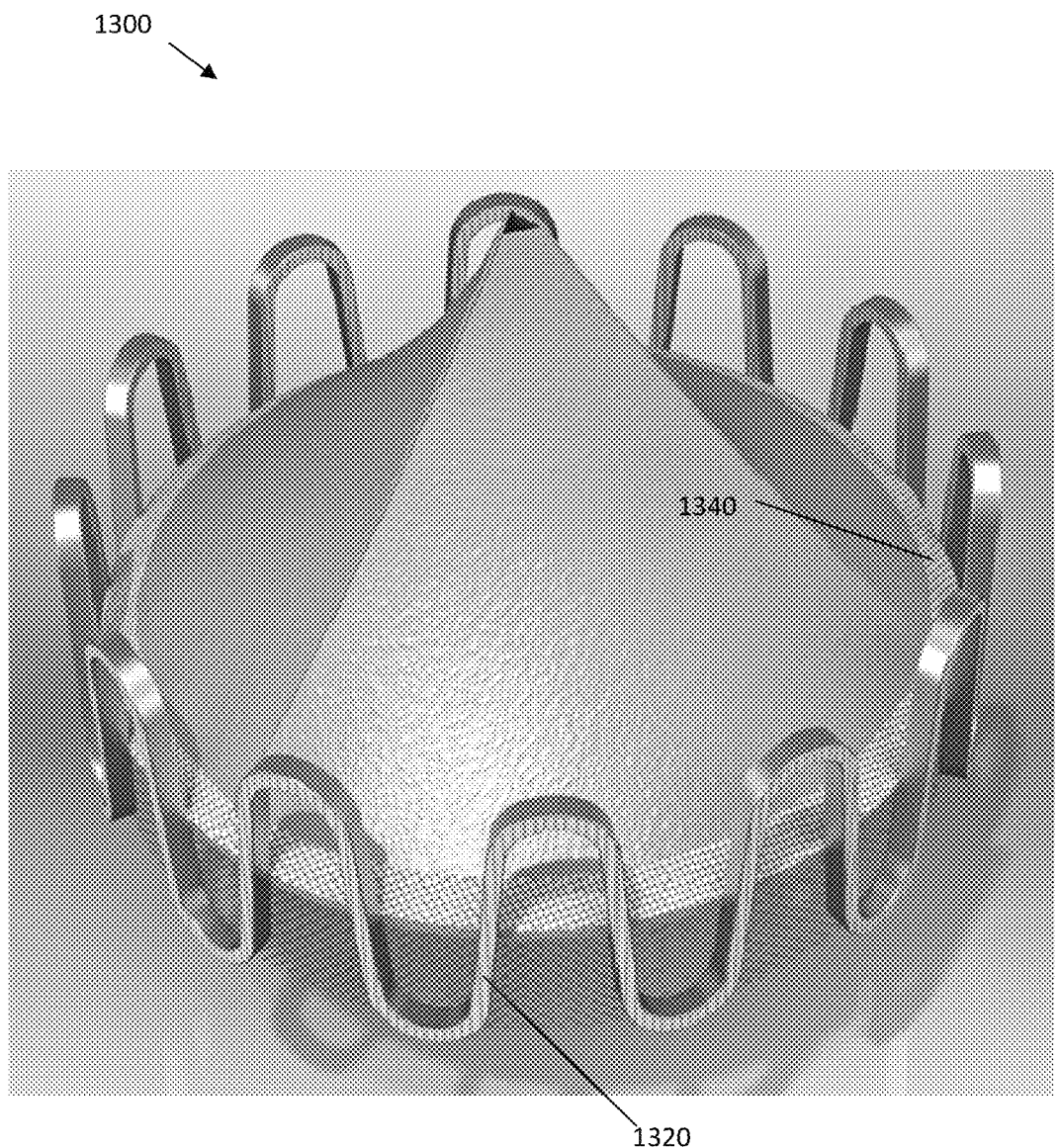
FIG. 13a is an illustration of a heart valve with grooves and noncontiguous dots.
Figure 13B:
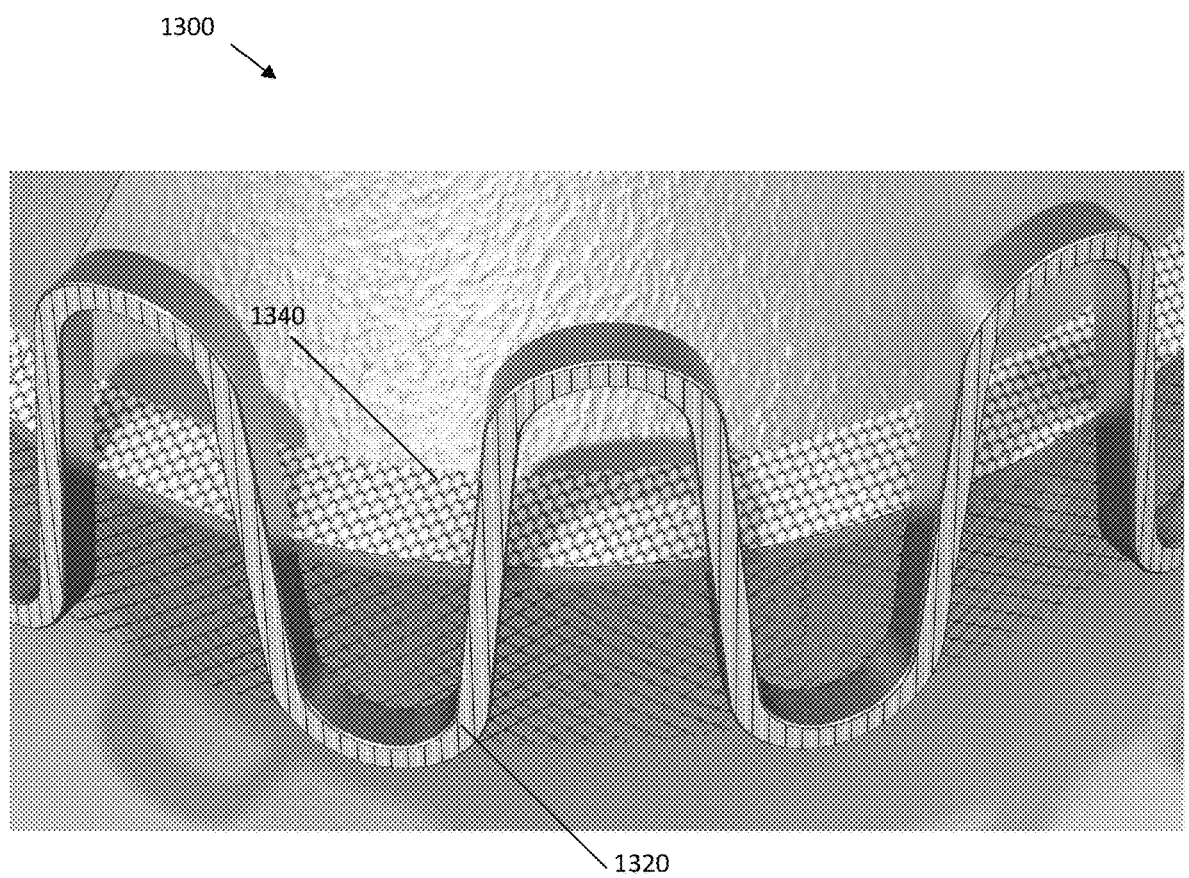

FIG. 13a depicts one embodiment of a textured heart valve 1300 having topographical features created thereupon. The heart valve 1300 has a portion imparted with a grooved texture 1320 to promote cell growth where the heart valve 1300 is anchored to the tissue, and a portion imparted with a dotted texture or noncontiguous elliptical pattern 1340 to pin the cells so they don't proliferate into the valve portion of the heart valve 1300. In the depicted embodiment, the grooves run along the length of the struts on the heart valve 1300, to provide directional migration of cells and thereby promote cell growth along and into the portion of the implant 1300 that is anchored into the heart of a patient. The portion of the heart valve 1300 having a noncontiguous elliptical pattern 1340 serves to halt the proliferation of cell growth such that the cell growth does not continue into the valve portion. The ideal texture for the cell growth may be a crosshatch to add an anchoring effect to the heart valve 1300. FIG. 13b is an enlarged view of the grooved portion 1320 and dotted portion 1340 of the heart valve 1300. In alternative embodiments, the features of the grooved portion 1320 may have different arrangements and/or shapes, such as grooves that run diagonally, grooves that run helically, complex geometries that promote cell growth along the length of the implant, features having multiple depths, and/or the like. The portion of the heart valve 1300 having a dotted texture 1340 may comprise divots, pores, holes, wells, and/or the like, serving to pin cells in place and thereby demote cell proliferation beyond the dotted portion 1340. In alternative embodiments, the features of the dotted portion 1340 may have different arrangements and/or shapes, or the portion may have greater or lesser width or height.

In still further alternative embodiments of the present invention, the devices modified could be more "industrial" in nature, rather than being medical devices. One such example is an earring post or stem (or other piercing articles), which may have its surface modified with a noncontiguous pattern of topographical features to prevent hole closure, infection, etc.

All documents and references cited herein are incorporated by reference in their entireties.

It is to be understood that the invention is not limited to the exact details of construction, operation, exact materials, or embodiments shown and described, as obvious modifications and equivalents will be apparent to one skilled in the art. Accordingly, the invention is therefore to be limited only by the scope of the appended claims.

What is claimed:

1. An implantable medical device having at least one fluid or tissue contacting surface, a depth defined by sidewalls of the implantable medical device, and a longitudinal axis, comprising:
   a plurality of elongate grooves in the fluid or tissue contacting surface, at least some of the plurality of elongate grooves further having groove endpoints that are oriented orthogonally relative to a longitudinal axis of an elongate groove having a groove endpoint; and
   a plurality of pores in the fluid or tissue contacting surface, at least some of the plurality of pores being in proximity to the groove endpoints.

2. The implantable medical device according to claim 1, wherein some of the plurality of elongate grooves are positioned in the sidewalls of the implantable medical device and extend parallel to plurality of elongate grooves in the fluid or tissue contacting surface of the implantable medical device.

3. The implantable medical device according to claim 2, further comprising a plurality of pores in the sidewalls of the implantable medical device.

4. The implantable medical device according to claim 3, wherein the plurality of pores in the sidewalls of the implantable medical device are positioned in proximity to the elongate grooves in the sidewalls of the implantable medical device.

5. The implantable medical device of claim 1, further comprising an intravascular stent or stent-graft.

6. The implantable medical device of claim 5, wherein the plurality of grooves are disposed along a majority of the fluid or tissue contacting surface of the implantable medical device.

7. The implantable medical device of claim 1, wherein at least some of the plurality of elongate grooves have a length of at least 0.1-5.0 microns.

8. The implantable medical device according to claim 2, wherein some of the elongate grooves are positioned in the sidewalls of the implantable medical device and extend orthogonally to the plurality of elongate grooves in the sidewalls of the implantable medical device.

* * * * *